US008969080B2

(12) United States Patent
Bergmann et al.

(10) Patent No.: US 8,969,080 B2
(45) Date of Patent: Mar. 3, 2015

(54) REMEDY FOR THE TREATMENT OF CARDIO-VASCULAR DISEASES OR DISORDERS

(75) Inventors: Martin Bergmann, Hamburg (DE); Joerg Huelsken, Denges (CH); Walter Birchmeier, Schwanebeck (DE); Makoto Mark Taketo, Kyoto (JP)

(73) Assignee: Max-Delbrueck-Centrum fuer Molekulare Medizin, Berlin (DE)

(*) Notice: Subject to any disclaimer, the term of this patent is extended or adjusted under 35 U.S.C. 154(b) by 723 days.

(21) Appl. No.: 12/573,281

(22) Filed: Oct. 5, 2009

(65) Prior Publication Data

US 2010/0255041 A1 Oct. 7, 2010

Related U.S. Application Data

(63) Continuation-in-part of application No. PCT/EP2008/002825, filed on Apr. 7, 2008.

(30) Foreign Application Priority Data

Apr. 5, 2007 (EP) .................... 07090071
May 9, 2007 (EP) .................... 07090096
Jan. 4, 2008 (EP) .................... 08000095

(51) Int. Cl.
A61K 48/00 (2006.01)
A61K 31/203 (2006.01)
A01K 67/027 (2006.01)
A61K 31/405 (2006.01)
A61K 31/415 (2006.01)
A61K 31/711 (2006.01)
A61K 38/17 (2006.01)
C07K 14/47 (2006.01)
C12N 15/85 (2006.01)

(52) U.S. Cl.
CPC .......... *A61K 31/203* (2013.01); *A01K 67/0276* (2013.01); *A61K 31/405* (2013.01); *A61K 31/415* (2013.01); *A61K 31/711* (2013.01); *A61K 38/1709* (2013.01); *C07K 14/4702* (2013.01); *C12N 15/8509* (2013.01); *A01K 2217/075* (2013.01); *A01K 2217/206* (2013.01); *A01K 2227/105* (2013.01); *A01K 2267/0375* (2013.01); *A61K 48/00* (2013.01)
USPC ............... 435/377; 435/325; 435/375

(58) Field of Classification Search
CPC .... A61K 31/203; C07K 14/4702; C12N 5/00; C12N 5/09
USPC .......................... 435/325, 375, 377
See application file for complete search history.

(56) References Cited

FOREIGN PATENT DOCUMENTS

| DE | 199 44 404 A1 | 3/2001 |
| WO | 99/02179 A1 | 1/1999 |
| WO | WO 0128548 A1 * | 4/2001 |
| WO | 2004/024901 A1 | 3/2004 |
| WO | WO 2004094610 A2 * | 11/2004 |

OTHER PUBLICATIONS

Fisch et al. Circulation, Oct. 2004, vol. 110, 17, Suppl. S, pp. 262-263.*
Leenders et al. Cirulation, 2006, vol. 114;II_13.*
Schroder et al. Expert Opinion Biol. Ther. 2004, vol. 4, No. 9, pp. 1413-1422. (Only Abstract provided.).*
Matsura et al. vol. 279, No. 12, Issue of Mar. 19, pp. 11384-11391, 2004.*
Holmes et al. Stemcells 2007;25:1339-1347.*
Sakoguchi-Okdada et al. Biochem Pharmacol. May 1, 2007;73(9):1318-29. Epub Jan. 5, 2007.*
Moon et al.: "WNT and beta-catenin Signalling: diseases and therapies." in Nature Review Genettics, vol. 5, Sep. 2004, pp. 689-699.
Li Ping et al: "Alterations of Axin protein expression during cardiac remodeling in rats." in Shengli Xuebao, vol. 55, No. 3, 25, Jun. 25, 2003, pp. 331-335.
Kimelman et al: "beta-catenin destruction complex: insights and questions from a structural perspective." in Oncogene, vol. 25, No. 57, Dec. 4, 2006, pp. 7482-7491.
Barandon et al: "Reduction of infarct size and prevention of cardiac rupture in transgenic mice overexpression FrzA" in Circulation, American Heart Association, Dallas, TX, US, vol. 108, No. 18, Nov. 4, 2003, pp. 2282-2289.
White et al: "Risk of cardiovascular events in patients receiving celecoxib: A meta-analysis of randomized clinical trials" in American Journal of Cardiology, vol. 99, No. 1, Jan. 2007, pp. 91-98.
Au et al: "Caleyelin binding protein promotes DNA synthesis and differentiation in rat neonatal cardiomyocytes" in Journal of Cellular Biochemistry, vol. 98, No. 3, Jun. 2006, pp. 555-566.
Van Gijn et al: "The wnt-frizzled cascade in cardiovascular disease." in Cardiovascular Research Jul. 2002, vol. 55, No. 1, pp. 16-24.
Barandon et al: "Frizzled A, a novel angiogenic factor: promises for cardiac repair." in European Journal of Cardio-Thoracic Surgery : Official Journal of the European Association for Cardio-thoracic Surgery Jan. 2004, vol. 25, No. 1, Jan. 2004, pp. 76-83.
Hart et al: "Downregulation of beta-catenin by human Axin and its association with the APC tumor suppressor, beta-catenin and GSK3beta" in Current Biology, vol. 8, No. 10, May 7, 1998, pp. 573-581.
Bergmann: "β-catenin depletion enhances cardiac endogenous regeneration" presented at the ESC Congress 2008 (European Society of Cardiology Congress 2008) on Sep. 1, 2008 in Munich. Published on the internet on Sep. 3, 2008, available at http://spo.escardio.org/eslides/view.aspx?eevtid=24&id=3340.

(Continued)

*Primary Examiner* — Janet Epps-Smith
(74) *Attorney, Agent, or Firm* — Joyce von Natzmer; Agris & von Natzmer, LLP

(57) ABSTRACT

Disclosed is the use of inhibitors of β-catenin expression or activity or modulators downregulating β-catenin expression or activity for the treatment of cardiovascular diseases or disorders and their use in the treatment of cardiovascular diseases and disorders, such as heart failure syndrome. The use of those agents resulted in particular in cardiomyocyte differentiation of endogenous cardiac stem cells.

26 Claims, 14 Drawing Sheets

(56) References Cited

OTHER PUBLICATIONS

Zelarayan et al.: "β-catenin downregulation attenuates ischemic cardiac remodeling through enhanced resident precursor cell differentiation" presented at a congress of the American Heart Association on Nov. 10, 2008 in New Orleans, LA.

Bergmann.: "β-catenin and adpative cardiac remodeling" presented at a conference in Nizza on Jun. 15, 2008. (Nizza, Italy, Europe).

* cited by examiner

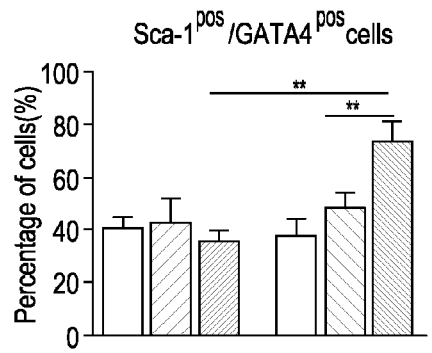
FIG. 12A
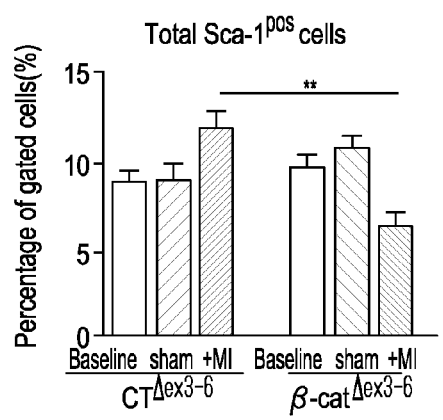
FIG. 12B
FIG. 12C
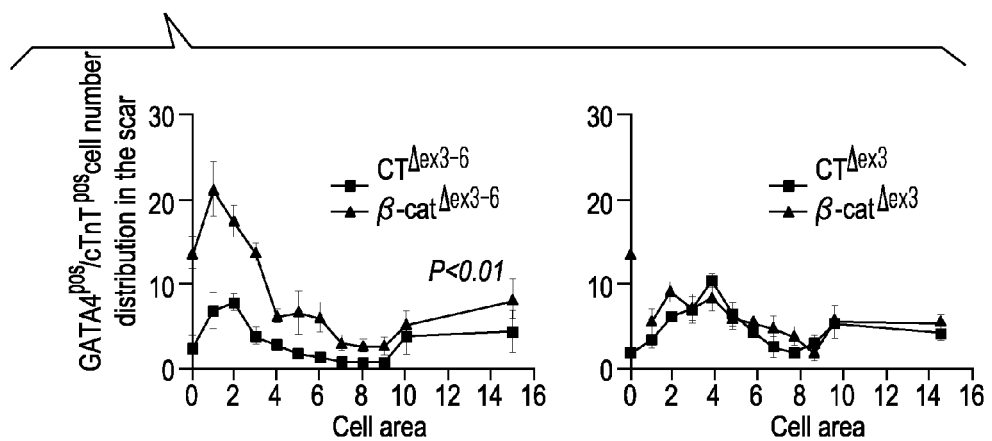
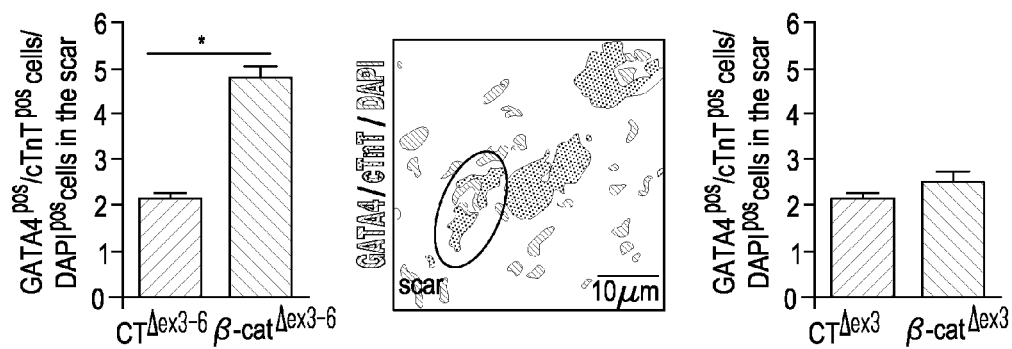

REMEDY FOR THE TREATMENT OF CARDIO-VASCULAR DISEASES OR DISORDERS

CROSS-REFERENCE TO RELATED APPLICATIONS

This application is a continuation-in-part of international application no. PCT/EP2008/002825, filed Apr. 7, 2008 and which claims priority to European Patent application nos. EP07090071.7, filed Apr. 5, 2007, EP07090096.4, filed May 9, 2007, and EP 08000095.3, filed Jan. 4, 2008.

FIELD OF THE INVENTION

The invention is directed at the use of inhibitors of β-catenin expression or activity or modulators downregulating β-catenin expression or activity. These inhibitors/modulators are in particular used to enhance cardiomyocyte differentiation of endogenous cardiac stem cells, in particular $GATA^{pos}$ endogenous cardiac stem cells, preferably in the treatment of heart failure syndrome(s).

BACKGROUND OF THE INVENTION

Beta-catenin (β-catenin) is a member of the plakophilin protein family. The plakophilins belong to the armadillo-related proteins, which are components of the desmosomal plaque. In addition to their adhesive function, the plakophilin β-catenins have been ascribed an important signaling function. For instance, β-catenin is a transcriptional co-activator of the T cell factor/lymphoid enhancer factor (TCF/LEF) complex that regulates embryonic, postnatal, and oncogenic growth in many tissues, including the heart (Brembeck et al. *Curr Opin Genet Dev.* 2006; 16:51-59).

The publications and other materials, including patents and patent publications referenced herein, are incorporated herein by reference in their entirety.

Cardiomyocyte growth occurs during left ventricular (LV) remodeling following chronic pressure overload and/or ischemic heart disease. Increased β-catenin levels were detected in the intercalated disc in heart specimens from patients with inherited cardiac hypertrophy (Masuelli et al. *Cardiovasc Res.* 2003; 60:376-387).

The β-catenin increase at the cell membrane was accompanied by reduced nuclear β-catenin levels.

LV remodeling includes re-activation of the fetal gene program and possibly the embryonic gene program as well (Liang et al. *J Mol Cell Cardiol.* 2002; 34:611-616). WNT/β-catenin regulation is one of the earliest events in cardiac development. Specifically, β-catenin downregulation following inhibitory Dickkopf signaling in the embryonic endoderm precedes cardiac development from the embryonic mesoderm (Lickert et al. *Dev Cell.* 2002; 3:171-181). Since universal β-catenin deletion is lethal, inducible tissue-specific modulation of β-catenin has been used to analyze the role of this factor in adult heart LV remodeling.

Two more recent publications have analyzed the effect of β-catenin depletion in the adult heart: Zhou et al. (*Am J Physio/Heart Circ Physiol.* 2007; 38:120) found no phenotype concerning membrane function due to the compensatory upregulation of plakoglobin in the intercalated disc as previously described in other tissues (Huelsken et al. *Cell.* 2001; 105:533-545). Chen et al. (*Mol. Cell. Biol.* 2006; 26:4462-4473) confirmed their previous in vitro observations concerning β-catenin in adult cardiac hypertrophy: the increase in heart weight/body weight after trans-aortic constriction was attenuated in β-catenin depleted transgenic mice.

WO 2004/094610 A2 discloses a system, method and compositions related to cardiomyocyte differentiation from a non-cardiomyocyte cell using factors that activate WNT/β-catenin-signaling. The invention is said to relate to a cell-therapy system, in which a cell the WNT/β-catenin signaling pathway is activated and this cell or a cell tissue resulting from this cell is used for the therapy of cardiac failure.

The report of Barandon et al. (*Circulation* 2003; 108:2282-2289) investigates the role of the soluble Frizzled related protein A, sFRP A, as a regulator of healing processes after myocardiac infarction. Generally, soluble frizzled related proteins are able to inhibit WNT-signaling with its downstream target β-catenin. By overexpressing sFRP A in transgenic mice they demonstrated that cardiac function is improved. Although this report shows a correlation between overexpression of sFRP A and a decrease of cytosolic β-catenin after myocardiac infarction, the authors are not able to directly trace back the improvement of cardiac function to the decrease of cytosolic β-catenin. The only conclusion that could be drawn from this study is that blocking WNT-signaling by sFRP A results in reduced infarct size and cardiac rupture. No conclusion about the role of β-catenin can be drawn as many different factors upstream of β-catenin are involved in WNT-signaling and may contribute to the observed effect. Furthermore WNT-dependent signaling can involve other, alternative mediators (Liu et al. *Cell* 2002; 108:837-847). Thus, no link has been established to the role of β-catenin in enhancing endogenous cardiac regeneration. In their discussion the authors conclude that the effect of overexpressing sFRP A is independent from β-catenin.

In sum, the exact role of β-catenin in adult cardiac remodeling in vivo is still not understood: It is unclear, which effect the modulation of β-catenin expression in the heart has and which mechanism might be involved.

Thus, there remains a need to provide alternative methods and agents for the targeted and/or specific treatment of cardiovascular diseases or disorders, especially by cardiac regeneration. There is in particular a need for treating heart failure syndrome(s).

There is also a need to provide a heart medication for the specific treatment of cardiovascular diseases or disorders.

SUMMARY OF THE INVENTION

The present invention is directed at the use of agents capable of downregulating β-catenin dependent signaling for the treatment of cardiovascular diseases or disorders. As shown in the examples and figures, the specific inhibition of β-catenin dependent signaling by downregulating or inhibiting the expression or activity of β-catenin results surprisingly in adaptive cardiac hypertrophy that is protective for example after angiotensin-II (AngII) induced stress.

The present invention is also directed at a method for treating heart failure syndrome by administering to a subject in need thereof an inhibitor of β-catenin expression or activity or a modulator downregulating β-catenin expression or activity in an β-catenin expression or activity downregulating effective amount, wherein the administration is targeted towards cardiac cells or tissues; and wherein said administration results in enhanced cardiomyocyte differentiation of endogenous cardiac stem cells, preferably $GATA^{pos}$ endogenous cardiac stem cells.

The endogenous cardiac stem cells may be $\alpha MHC^{pos}$ resident cardiac precursor cells and express transcription factors including, e.g., Tbx5.

The invention is also directed at a method for treating heart failure syndrome comprising:
administering to a subject in need thereof an inhibitor of β-catenin expression or activity or a modulator downregulating β-catenin expression or activity in an β-catenin expression or activity downregulating effective amount, wherein the administration is targeted towards cardiac cells or tissues; and wherein said administration results in re-expression of transcription factors including at least Tbx5 and/or GATA4 in αMHG$^{pos}$ resident cardiac precursor cells and enhancement of differentiation of said resident cardiac precursor cells. The invention is also directed at the use of an agent that inhibits or downregulates β-catenin signaling or β-catenin expression or activity for the preparation of a remedy for the treatment of cardiovascular diseases or disorders.

Another aspect of the present invention is a heart medication comprising an agent capable of downregulating β-catenin dependent signaling in cardiac cells and/or tissues, preferably an inhibitor of β-catenin expression or modulator capable of downregulating β-catenin expression.

A method for the treatment of cardiaovascular diseases by application/administration of an agent for downregulating and/or inhibiting β-catenin expression or activity in cardiac cells or tissues is also an aspect of the present invention. This method comprises, in certain embodiments, direct application, e.g., injection of the agent into the heart.

In a preferred embodiment of the present invention the cardiovascular diseases are selected from the group of heart failure syndromes on the basis of chronic hypertension, ischemia, cardiac infarction, myocarditis and genetic causes. For those skilled in the art it is obvious that any other disease or disorder related to cardial cells or tissues are also within the scope of the present invention, comprising vascular or cellular damage as the basis for heart failure. Explicitly such diseases include those of the pericardium, heart valves, myocardium, blood vessels and veins. Furthermore a person skilled in the art knows that the present invention is applicable for mammals, especially humans.

The above referenced agent may be an inhibitor of β-catenin expression or activity or a modulator downregulating β-catenin expression or activity. Downregulating β-catenin dependent signaling constitutes one aspect of the invention.

In further aspects of the invention, the inhibitor or modulator is an expression construct that is transferred into the cardiac tissue or cells. A preferred method for delivering the expression construct into the cell is transfection. Known substances for facilitating transfer of the expression construct through the cell membrane may be employed and are within the scope of the present invention.

Genetic material comprising nucleic acids, polynucleotides, RNA and DNA, of either natural or synthetic origin, including recombinant RNA and DNA and antisense RNA and DNA; hammerhead RNA, ribozymes, antigene nucleic acids, both single and double stranded RNA and DNA and analogs thereof, either in combination or not with other elements such as, for example, without limitation, cardiac tissue or cell specific enhancers, and nuclear localization signals, can be introduced into eukaryotic cells or organisms/patients via transformation or transfection techniques. The present invention uses an "expression construct", "nucleic acid construct" or alternatively a "nucleotide construct" or alternatively a "DNA construct". The term "construct" is used herein to describe a molecule, such as a polynucleotide which may optionally be chemically bonded to one or more additional molecular moieties, such as a vector, or parts of a vector. In a specific—but by no means limiting—aspect, a nucleotide construct is exemplified by a DNA expression constructs suitable for the transformation of a cardiac host cell. As used herein, the terms "transformation" and "transfection" are intended to refer to a variety of art-recognized techniques for introducing foreign nucleic acid into a host cell/or tissue, including, for example, but not limited to, calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals. For stable transfection of mammalian cells, it is known that, depending upon the expression vector and transfection technique used, only a small fraction of cells may integrate the foreign DNA into their genome.

In order to obtain efficient in vivo transfer of the bioactive therapeutic agent of the present invention, various transfection agents may be employed. Representative examples of transfection agents which are suitable for use with the methods of the present invention include, but are not limited to, calcium phosphate or calcium chloride co-precipitation, DEAE-dextran-mediated transfection, quaternary ammonium amphiphile DOTMA ((dioleoyloxypropyl)trimethylammonium bromide). Lipophilic glutamate diesters with pendent trimethylammonium heads; the metabolizable parent lipids such as the cationic lipid dioctadecylamido glycylspermine (DOGS) and dipalmitoylphosphatidyl ethanolamylspermine (DPPES); metabolizable quaternary ammonium salts (DOTB, N-(1-[2,3-dioleoyloxy]propyl)-N, N,N-trimethylammonium methylsulfate (DOTAP), polyethyleneimine (PEI), dioleoyl esters, ChoTB, ChoSC, DOSC); 3beta[N—(N',N'-dimethylaminoethane)-carbamoyl]cholesterol (DC-Chol), dioleoylphosphatidyl ethanolamine (DOPE)/3beta[N—(N',N'-dimethylaminoethane)-carbamoyl]cholesterolDC-Chol in one to one mixtures, spermine, spermidine, lipopolyamines, lipophilic polylysines (LPLL), [[(1,1,3,3-tetramethylbutyl)cresoxy]ethoxy]ethyl]dimethylbenzylamio-nium hydroxide (DEBDA hydroxide) with excess phosphatidylcholine/cholesterol, cetyltrimethylammonium bromide (CTAB)/DOPE mixtures, lipophilic diester of glutamic acid (TMAG) with DOPE, CTAB, DEBDA, didodecylammonium bromide (DDAB), and stearylamine in admixture with phosphatidylethanolamine, DDAB/DOPE (TransfectACE, GIBCO BRL), and oligogalactose bearing lipids. Also encompassed within the present invention is the use of various transfection enhancer agents to increase the efficiency of transfer of the bioactive therapeutic factor/agent (i.e., e.g., an inhibitor and/or an modulator as described herein) into cells. Suitable transfection enhancer agents include, for example, without limitation, DEAE-dextran, polybrene, lysosome-disruptive peptide, chondroitan-based proteoglycans, sulfated proteoglycans, polyethylenimine, polylysine, integrin-binding peptide CYGGRGDTP, linear dextran nonasaccharide, glycerol, cholesteryl groups tethered at the 3'-terminal internucleoside link of an oligonucleotide, lysophosphatide, lysophosphatidylcholine, lysophosphatidylethanolamine, and 1-oleoyl lysophosphatidylcholine.

The expression constructs according to the present invention encode, in a preferred embodiment, proteins inhibiting or downregulating β-catenin expression or activity. The interference with β-catenin expression or activity through the encoded proteins may be mediated by direct interaction or indirectly.

Preferred proteins encoded by the expression construct for the use according to the invention are Axin, Axin2, Chibby, Dapper, Human naked cuticle, soluble frizzled-related protein A, Dickkopf, Nemo-like kinase or Inhibitor of β-catenin (ICAT) or members of the Krüppel-like-factors (KLF), especially KLF15.

The agents are in one embodiment proteins that specifically target serin/threonin residues of β-catenin necessary for GSK3-β phosphorylation inducing subsequent degradation of β-catenin. These residues are preferably all localized in the N-terminal end of β-catenin coded by exon3, namely serine 33, serine 37, threonin 41 and serine 45. Kinases enhancing phosphorylation of these sites are also preferred proteins encoded by the expression constructs as they will lead to reduced cellular β-catenin levels.

As it is known to those skilled in the art, the COOH-terminal end of the "inhibitor of β-catenin and TCF" (ICAT) binds to the groove formed by armadillo repeats 5 to 9 of β-catenin. This site is known to be instrumental for the binding to the transcription factor TCF and E-cadherin. Any other proteins blocking this site will also inhibit β-catenin dependent transcription and are therefore potentially useful in enhancing cardiac repair in heart failure. Especially casein kinase 1 (CK1) also enhances β-catenin degradation and is therefore a potentially useful therapeutic agent in cardiovascular disease.

In further aspects of the invention, upstream inhibitors of the WNT/β-catenin pathway, such as members of the group of soluble frizzled-related proteins (sFRP) like FrizzledA (FrzA) and other inhibitory Wnt signals, are also preferred proteins to negatively influence expression or activity of β-catenin. FrzA was shown to prevent cardiac rupture after experimental myocardiac infarct in mice (L. Barandon et al., Circulation 2003; 108:2282-89) by enhancing capillary density and reducing infarct size. Other upstream inhibitors that may be useful in cardiac regeneration are the following proteins and their homologs: dickkopf-1 (Dkk), Frizzled B, nemo-like kinase (NLK), proteins enhancing NLK activity like "kruppel like factor—15 (KLF15)", inhibitors of bcl9, activators of βTrCP.

The person skilled in the art will readily understand that inhibition or downregulation of β-catenin expression or activity can be achieved by cellular expression of the expression constructs and the encoded proteins. Alternatively, soluble forms of the above mentioned proteins may be specifically targeted to cardiac cells or tissues. For specific delivery of the agent to cardiac cells or tissues the agent may be optionally encapsulated in a carrier targeted to cardiac cells or tissues. Additionally, the carrier can be "opened" by external measures like supersonic pulse resulting in release of the encapsulated agent. These measures are also preferred within therapeutic use of the agent to achieve release at a defined point in time during therapy. The person skilled in the art readily understands that a carrier can contain more than one agent and subsequent release of the agents can be achieved.

To assure cardiac-specific expression of the expression constructs of β-catenin inhibitors (direct or indirect), promoters like the α-myosin heavy chain (αMHC) and myosin light chain 2c (MLC2v) promoter are preferred. Cardiac-specific expression is desirable as it is likely that unspecific inhibition of β-catenin in various cells or tissues not belonging to the heart or vessels related to the supply of cardiac cells or tissues may cause severe side-effects. The expression control elements may also be, in certain embodiments, inducible, for instance by hormones or antibiotics. Immunoconjugates comprising antibodies or other targeting agents directed heart cells coupled to the inhibitor of β-catenin expression or activity or a modulator downregulating β-catenin expression or activity are also within the scope of the present invention (see, e.g, U.S. Pat. No. 7,348,004).

Furthermore expression constructs of the present invention are targeted at β-catenin expression control elements. Those elements are preferably deoxyribonucleic acid sequences controlling β-catenin gene transcription, such as promoters or other β-catenin specific gene transcription control elements.

Preferably, the expression constructs are plasmids. The expression construct may also be an adenoviral vector, an adenoassociated vector, a retroviral vector or a lentiviral vector.

The term "vector" refers to a nucleic acid molecule capable of transporting another nucleic acid to which it has been linked. The term "expression vector" or "expression construct" includes any vector, (e.g., a plasmid, cosmid, phage or artificial chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions.

Also contemplated within the present invention is the use of a virus-like particle containing a bioactive therapeutic agent according to the invention, wherein the virus-like particle is physically linked to the transfection agent, which is also linked to the microparticle. Such virus-like particles may be designed using polyethylenimine (PEI) conjugated to a therapeutic sequence. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

Another aspect is the use of an expression construct for in vivo gene targeting, wherein the in vivo gene targeting is preferably mediated through the expression of small interference RNA targeted to β-catenin RNA. One way of inhibiting gene expression is based on the production of double-stranded RNA molecules. Using such double-stranded RNA (dsRNA), targeted switching off of single genes is possible in a highly effective manner and more rapidly compared to any other method, without impeding protein formation of neighboring genes. The basic principle is referred to as RNA interference, abbreviated as RNAi, and the dsRNA sequence responsible for this phenomenon as siRNA (small interference RNA).

The siRNA does not prevent reading of the gene, but rather switches on a cellular mechanism causing degradation of the mRNAs read from the gene, thus preventing formation of the corresponding protein (post-transcriptional gene silencing).

Furthermore the use of so-called "decoy" oligonucleotides is intended to block transcription of the β-catenin gene. These oligonucleotides mimic the consensus sequence of transcription factors and as they are recognized and bound by the factor, they occupy the transcription factor's DNA-binding site. Consequently the transcription factor is no longer able to bind its consensus sequence within the promoter and will not positively effect the transcription of the corresponding gene.

Another embodiment of the present invention is the use of an expression construct that is covalently linked to signaling elements specific for cardiac cells or tissue. As already mentioned the scope of the present invention is directed to the inhibition of β-catenin expression or activity in cardiac cells or tissues. To assure specific delivery of expression constructs cardiac cell or tissue specific signaling elements may be used.

Standard techniques for the construction of expression vectors suitable for use in the present invention are well-known to those of ordinary skill in the art and can be found in such publications as Sambrook et al. (1989) Molecular Cloning: A Laboratory Manual, 2nd Ed. Cold Spring Harbor, N.Y. A variety of strategies are available for ligating fragments of DNA, the choice of which depends on the nature of the termini of the DNA fragments and which choices can be readily made by the skilled artisan.

The recombinant expression vectors of the invention may be specifically designed for expression of a polypeptide in eukaryotic cells (e.g., insect cells (using baculovirus expression vectors), yeast cells, or mammalian cells, or in an organism). These cells may be used as drugs or pharmaceutical compositions in gene therapy. Suitable host cells are discussed further in Goeddel, supra.

In a preferred embodiment, a nucleic acid is expressed in mammalian cells or an organism using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in cardiac cells or tissues. Tissue-specific regulatory elements are known in the art.

The term "gene delivery" or "gene transfer" refers to methods or systems for reliably inserting foreign DNA into target cells, such as into muscle cells or others. Such methods can result in transient or long term expression of genes. The amount of viral vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian or non-mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

In addition to virus-mediated gene-delivery systems, there are several nonviral options for gene delivery. The simplest method is the direct introduction of therapeutic DNA into target cells. This approach is limited in its application because it can be used only with certain tissues and requires large amounts of DNA.

Another non-viral approach involves the creation of an artificial lipid sphere with an aqueous core. This liposome, which carries the therapeutic DNA, is capable of passing the DNA through the target cell's membrane.

Therapeutic DNA also can get inside target cells by chemically linking the DNA to a molecule that will bind to special cell receptors. Once bound to these receptors, the therapeutic DNA constructs are engulfed by the cell membrane and passed into the interior of the target cell. This delivery system tends to be less effective than other options.

Persons skilled in the art are also experimenting with introducing a $47^{th}$ (artificial human) chromosome into target cells. This chromosome would exist autonomously alongside the standard 46—not affecting their workings or causing any mutations. It would be a large vector capable of carrying substantial amounts of genetic code, and scientists anticipate that, because of its construction and autonomy, the body's immune systems would not attack it. A problem with this potential method is the difficulty in delivering such a large molecule to the nucleus of a target cell.

Another aspect of the present invention is directed at known inhibitors of β-catenin and their use for downregulation or inhibition of β-catenin expression or activity in cardiac cells or tissues. The use of 13-cis-retinoic-acid, indometacin, PKF 118-310, Celecoxib, SKI-606 and Quercitin are preferred.

In further aspects the agent is selected from the group of proteins, peptides, antibodies, nucleic acids or small molecules.

The invention also relates to a pharmaceutical composition, comprising the gene therapy construct of the invention and a pharmaceutically acceptable carrier.

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention in an effective amount may be dissolved or dispersed in a pharmaceutically acceptable carrier or aqueous medium. Such compositions also are referred to as inocula. The phrase pharmaceutically or pharmacologically acceptable refers to molecular entities and compositions that do not produce adverse, allergic, or other untoward reactions when administered to an animal or a human. As used herein, pharmaceutically acceptable carrier, includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

The preparation of a pharmacological composition that contains an agent for the use according to the invention dissolved or dispersed therein is well understood in the art.

Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active agent can be mixed with excipients which are pharmaceutically acceptable and compatible with the active ingredient and in amounts suitable for use in the therapeutic methods described herein. Suitable excipients are, for example, water, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient.

The therapeutic pharmaceutical composition that contains an agent for the use according to the invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The above-mentioned physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

In addition to the active substance(s), i.e., the agent for the use according to the invention, solutions and emulsions may include conventional carriers such as solvents, solubilizers, and emulsifiers such as water, ethyl alcohol, isopropyl alcohol, ethyl carbonate, ethyl acetate, benzyl alcohol, benzyl benzoate, propylene glycol, 1,3-butylene glycol, dimethylformamide, oils, especially cotton seed oil, peanut oil, corn oil, olive oil, castor oil and sesame oil, glycerol, glycerol formal, tetrahydrofurfuryl alcohol, polyethylene glycols, and fatty esters of sorbitan, or mixtures of these substances. For parenteral application, the solutions and emulsions may also be present in a sterile and blood-isotonic form.

In addition to the active substance(s), suspensions may include conventional carriers such as liquid diluents, e.g. water, ethyl alcohol, propylene glycol, suspending agents, e.g. ethoxylated isostearyl alcohols, polyoxyehtylenesorbitol and sorbitan esters, microcrystalline cellulose, aluminum metahydroxide, bentonite, agar, and tragacanth, or mixtures of these substances.

Other examples for delivery of the agents for the use according to the present invention that may be employed include intra-arterial, intracavity, intravesical, intrathecal, intrapleural, and intraperitoneal routes.

Intra-arterial administration is achieved using a catheter that is inserted into an artery to an organ or to an extremity. Typically, a pump is attached to the catheter. Agents can be given directly via catheter.

A further aspect of the present invention relates to gene therapy and applications related to the prophylaxis, diagnosis, therapy, follow-up and/or aftercare of cardiac diseases.

As used herein, the term "effective amount" refers to the amount of inhibitor of β-catenin expression or activity or modulator downregulating β-catenin expression or activity that is sufficient to enhance cardiomyocyte differentiation of endogenous $GATA^{pos}$ cardiac stem cells (resident cardiac precursor cells) in the subject or cells that are subject to the administration. As the person skilled in the art will appreciate, the effective amount will differ with the route and/or form of administration, but can be readily determined by the person of skill in the art. For example, when treating of heart failure syndrome by direct injection into the heart/a heart region of a subject, an effective amount may refer to the amount of an agent required to enhance cardiomyocyte differentiation of endogenous cardiac stem cells (resident cardiac precursor cells) so that cardiomyocyte are formed from endogenous stem cells (cardiac precursor cells) as evidenced by the expression of relevant transcription factors and/or markers described herein. Fractional shortening is preferably improved by at least 5%, 10%, 20, 30 or 40% and/or infarct size is preferably reduced by at least 5%, 10%, 20%, 30% or 40%.

BRIEF DESCRIPTION OF THE FIGURES

FIG. 12A-G β-Catenin depletion enhances cardiomyocyte differentiation of Sca-1$^{pos}$ precursor cells following experimental infarct.

DETAILED DESCRIPTION OF VARIOUS AND PREFERRED EMBODIMENTS OF THE INVENTION

Figure 1A:
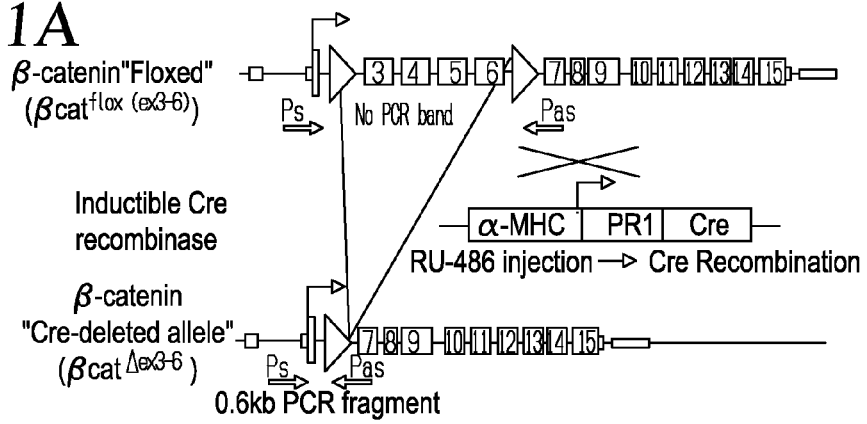
FIG. 1A-E Generation of mice with inducible, heart specific β-catenin depletion (β-cat$^{\Delta ex3-6}$)

The present invention is based on findings that the depletion of β-catenin has a protective effect on the heart. Links between downregulation of β-catenin and effects like increased survival rate, reduction of infarct size or improvement of the heart's pump function have now been established.

The present invention relates in particular to inhibitors of β-catenin expression or activity or modulators downregulating β-catenin expression or activity and their use in the treatment of cardiovascular diseases or disorders, such as heart failure syndrome.

The present invention relates in particular to a method for stimulating cardiomyocyte differentiation of endogenous cardiac stem cells, preferably GATA$^{pos}$ endogenous cardiac stem cells via inhibitors of β-catenin expression or activity or modulators downregulating β-catenin expression or activity.

The inhibitors of β-catenin expression or activity or modulators downregulating β-catenin expression or activity according to the present invention are administered to a subject in need of therapeutic treatment or to cells, in particular cardiac cells, in particular those isolated from such a subject in need of therapeutic treatment.

As one example, quericitin is administered to a subject with heart failure syndrome based on cardiac infarction. In this example, quericitin is administered in soluble form intravenously to the subject so that it concentrates in heart cells. The amount administered is effective to enhance cardiomyocyte differentiation of GATA$^{pos}$ endogenous cardiac stem cells.

As a second example, an expression vector that expresses KLF15 is administered to the patient with heart failure syndrome based on cardiac infarction. In this example, the vector is administered in soluble form intravenously to the patient so that it concentrates in heart cells. KLF15 expression is regulated by the α-myosin heavy chain (αMHC) promoter to ensure cardiac specific expression. KLF15 concentrates in the heart cells. KLF15 effectively inhibits β-catenin dependent transcription in cardiomyocytes of the patient. The amount of vector administered is effective to enhance cardiomyocyte differentiation of GATA$^{pos}$ endogenous cardiac stem cells. Fractional shortening is improved significantly.

The role of β-catenin in adult heart homeostasis and LV remodeling after chronic GPCR-stimulation was studied. It was found that, relative to controls, decreased β-catenin expression caused modest cardiac hypertrophy at baseline. AngII (Angiotensin II) infusion induced cardiac hypertrophy both in control—and in β-catenin depleted mice, but not in β-catenin-stabilized mice. This decreased hypertrophic response was accompanied by reduced fractional shortening. The phenotype of deteriorating heart function upon β-catenin stabilization was associated with altered regulation of the T-box proteins Tbx5 and Tbx20 as well as the AKT-regulated, atrophy-related protein IGF-binding protein 5 (IGFBP5). It was concluded, that β-catenin downregulation is required for adaptive cardiac hypertrophy.

In particular, downregulation of β-catenin was found to initiate an adaptive cardiomyocyte hypertrophy in the adult heart. Stabilizing β-catenin in the adult heart blocks signaling pathways required for protective hypertrophy after AngII-induced stress. This effect was not associated with detectable changes in intercellular adhesion but with altered gene expression of Tbx5 and Tbx20, which belong to the cardiac embryonic gene program. This finding suggests that upon hypertrophic stress, the adult heart reverts to regulation of β-catenin in a fashion similar to β-catenin involvement in embryonic cardiac development.

The Sca-1$^{pos}$ (stem cell antigen 1) resident precursor cell population was found to exhibit an active αMHC-promoter and GATA4 expression, which confirms that these cells are committed to the cardiomyocyte lineage in the adult heart.

Modulating signaling cascades also governing LV embryonic cardiomyocyte differentiation such as the β-catenin pathway enhance endogenous regeneration. This is sufficient to significantly affect global LV function and survival following myocardial infarct.

Myocardial infarction (MI) is modeled in mouse, by ligation of the left anterior descending coronary artery (LAD). As will be detailed below, four weeks after chronic LAD ligation, small cells were observed in the scar of both control and β-catenin depleted mice. Apart from survival, left ventricular (LV) function was improved.

Associated with the functional improvement, LV scar cellularity was altered: β-catenin-depleted mice showed a marked subendocardial and subepicardial layer of small cTnT$^{pos}$ cardiomyocytes associated with increased expression of cardiac lineage markers Tbx5 and GATA4.

Microscopically, mice with β-catenin depletion exhibited a thin but complete lining of cTnT$^{pos}$ (cardiac troponin T pos) cells along the scar endocardium and epicardium, while control animals showed only scattered cTnT$^{pos}$ cells.

The enhanced cardiac differentiation was also observed to be associated with re-expression of embryonic cardiomyocyte transcription factors Tbx5, Tbx2 and GATA4.

In particular, in vivo, early cardiac transcription factors GATA4 and Tbx5 were upregulated upon β-catenin depletion in infarcted mice.

The herein presented in vivo and in vitro data supports that in the adult heart β-catenin depletion enhances differentiation of resident Sca-1$^{pos}$ cells committed to the cardiac lineage.

As the person skilled in the art will understand, this enhanced cardiomyocyte differentiation of endogenous cardiac stem cells, is highly significant for a variety of cardiovascular diseases, in particular heart failure syndrome(s).

The two complementary mouse models analyzed in the examples below were generated employing previously described β-catenin floxed transgenic mice. No apparent phenotype linked to the membrane function of β-catenin in complex with N-cadherin was observed. The compensatory upregulation of plakoglobin (γ-catenin) demonstrated by Zhou et al. (*Am J Physiol Heart Circ Physiol.* 2007; 38:120) in heart tissue might account for this phenomenon. This hypothesis is also supported by data from other tissues employing this very same floxed mouse strain (Huelsken et al. *Cell.* 2001; 105:533-545; Zhou et al. *Am J Physiol Heart Circ Physiol.* 2007; 38:120).

Similar considerations concerning the relevance of membrane-associated β-catenin versus nuclear β-catenin apply to the mouse model with β-catenin stabilization: while no apparent phenotype concerning rhythm disturbances or membrane dysfunction was observed, classical β-catenin target genes Axin2, Tcf-4 and Lef-1 were found upregulated in cardiac tissue extracts. The nuclear localization of the stabilized truncated β-catenin mutant in β-cat$^{exon3\ flox/flox}$ also accounts for other phenoytpes including the recently described block in haematopoetic stem cell differentiation (Harada et al. *EMBO J.* 1999; 18:5931-5942; Scheller et al. *Nat lmmunol.* 2006; 7:1037-1047).

It was surprising to find that by stabilizing β-catenin in the adult heart, the hypertrophic response after AngII stimulation was abrogated; however, this came at the price of deteriorating heart function. This observation contradicts earlier findings, where β-catenin depletion blocked cardiac hypertrophy after trans-aortic constriction (TAC) (Hag et al. *Proc Natl Acad Sci USA.* 2003; 100:4610-4615; Chen et al. *Mol. Cell. Biol.* 2006; 26:4462-4473).

Several differences between the studies may explain the discrepant findings: The AngII stimulus employed here activates signaling cascades different from pressure overload as in TAC. Discrepant results concerning the same signaling molecule have been described before i.e. concerning the role of MEKK1 in cardiac hypertrophy (Minamino et al. *Proc Natl Acad Sci USA*. 2002; 99:3866-3871; Sadoshima J et al. *J. Clin. Invest*. 2002; 110:271-279). In β-catenin depleted mice, Chen et al. describe an increase in heart weight and upregulation of hypertrophy markers ANP and β-MHC when compared to baseline levels indicating intact hypertrophy in β-catenin depleted mice. The definition of hypertrophy was based on heart weight and cardiomyocyte width of isolated cardiomyocytes; neither diastolic wall size or cell surface area in tissue sections were reported (Chen et al. *Mol. Cell. Biol.* 2006; 26:4462-4473). Intriguingly concerning the question of adaptive vs. mal-adaptive cardiac remodeling, β-catenin depleted mice preserved LV-function despite ongoing stress by TAC supporting a concept of adaptive hypertrophy mediated by β-catenin downregulation.

Another major difference between the studies is the time course of the experiments: for the experiments performed in the context of the present invention and that are described below, mice were stimulated with AngII 10 days after mifepristone-induced Cre recombinase activation and analyzed 2 weeks later; Chen et al. exposed their mice to TAC 6 weeks after induction of Cre recombinase and analyzed them 2 weeks later. The initial delay after β-catenin depletion might have induced secondary effects (Chen et al. *Mol. Cell. Biol.* 2006; 26:4462-4473).

The complimentary studies shown below employing mice with β-catenin stabilization seemingly confirm a beneficial role of β-catenin downregulation in cardiac hypertrophy: after AngII stimulation, the β-catenin-stabilized mice exhibited a deterioration of cardiac function. To the best of our knowledge, in vivo studies describing the phenotype of mice with genetic stabilization of β-catenin have not been described precedingly.

First, it has been tested whether cardiac β-catenin manipulation might affect cardiomyocyte apoptosis. While an increase of TUNEL/α-sarcomeric actin/DAPI positive nuclei after AngII treatment in control mice and β-catenin depleted mice to levels reported before was observed, this was not observed in the mice with β-catenin stabilization (van Empel et al. *Circ Res*. 2005; 96:e92-e101). While determination of absolute values of apoptosis would require the combination of several techniques, these data clearly exclude increased apoptosis to account for the observed phenotype. This observation is in line with previous findings: several studies analyzing tissue-specific alterations of β-catenin levels found that β-catenin regulated expression of survival genes in brain, thymocytes, and vascular smooth muscle cells (Wang et al. *Circ Res*. 2002; 90:340-347). The association of stabilized β-catenin and cell survival of isolated rat cardiomyocytes after activation of the PI3-kinase/AKT pathway has been previously described (Bergmann et al. *Journal of Molecular and Cellular Cardiology*. 2004; 37:681-690).

Next, previously described target genes of β-catenin and PI3kinase/AKT were analyzed. The PI3-kinase/AKT pathway was previously shown to control β-catenin levels in cardiomyocytes (Haq et al. *Proc Natl Acad Sci USA*. 2003; 100:4610-4615). As β-catenin downregulation initiates heart formation in the embryo, the gene expression levels of different transcription factors related to cardiomyocyte differentiation were investigated. Interestingly, differential regulation of T-box proteins Tbx5 and Tbx20 was found: AngII treatment downregulated Tbx5 mRNA and protein expression in control mice, whereas this effect was attenuated in β-cat$^{\Delta ex3}$ mice. Tbx20 was upregulated in mice with β-catenin stabilization. Different roles have been identified for these T-box proteins: Tbx5 was previously shown to promote cardiomyocyte differentiation in association with Nkx2.5 (Hiroi et al. *Nat Genet*. 2001; 28:276-280). In addition, heterozygote Tbx 5 deletion is a model for the Holt-Oran syndrome; interestingly, by 8 weeks after birth such mice develop a phenotype of diastolic dysfunction known to precede systolic dysfunction (Zhou et al. *Am J Physiol Heart Circ Physiol*. 2005; 289: H992-1001). In contrast, Tbx20 is known to exert multiple transcriptional repressive functions including inhibition of ANP expression (Stennard et al. *Development*. 2005; 132: 2451-2462; Plageman and Yutzey. *J. Biol. Chem.* 2004; 279: 19026-19034). Increased expression of Tbx20 might therefore inhibit cardiac growth in β-cat$^{\Delta ex3}$ mice.

In addition, the regulation of the IGF-binding protein 5 (IGFBP5) was observed. In general, IGFBP5 inhibits cell proliferation and differentiation but increases cell survival rates (Schneider et al. *J. Endocrinol*. 2002; 172:423-440). Upregulation of IGFBP5 has been detected in mouse models with chronic activation of AKT (Matsui et al. *J Biol Chem*. 2002; 277:22896-22901). Prolonged activation of this pathway was recently found to induce a phenotype of dilated cardiomyopathy (Shiojima et al. *J. Clin. Invest*. 2005; 115: 2108-2118; Nagoshi et al. *J. Clin. Invest*. 2005; 115:2128-2138). The known functions of IGFBP5 and its expression levels observed here make this protein another candidate for explaining the effect of β-catenin stabilization on cardiac left ventricular remodeling.

In sum, downregulation of β-catenin initiates adaptive cardiomyocyte hypertrophy in the adult heart. Stabilizing β-catenin in the adult heart blocks signaling pathways required for protective hypertrophy after AngII-induced stress. This effect was not associated with detectable changes in intercellular adhesion but with altered gene expression of Tbx5 and Tbx20, which belong to the cardiac embryonic gene program. This finding suggests that upon hypertrophic stress, the adult heart reverts to regulation of β-catenin in a fashion similar to β-catenin involvement in embryonic cardiac development.

By further experimentation, it was possible to determine that the Sca-1$^{pos}$ resident precursor cell population exhibits an active αMHC-promoter and GATA4 expression, which confirms that these cells are committed to the cardiomyocyte lineage in the adult heart. Modulating signaling cascades that also govern LV embryonic cardiomyocyte differentiation such as the β-catenin pathway enhance endogenous regeneration. This is sufficient to significantly affect global LV function and survival following myocardial infarct.

The role of β-catenin in adult cardiac remodeling after chronic LAD ligation was studied. Infarct mortality was ameliorated by β-catenin depletion already during the first two weeks. Similarly to this observation, ubiquitous overexpression of the Wnt signaling antagonist frizzledA resulted in reduced mortality between two and five days after permanent LAD ligation due to altered infarct healing (Brandon et al., Circulation 2003). Both studies suggest, that modification of the cellular scar composition already affects ventricular wall stability early on.

Four weeks after chronic LAD ligation the inventors observed small cTnT$^{pos}$ cells in the scar of both control and β-catenin depleted mice. Microscopically, mice with β-catenin depletion exhibited a thin but complete lining of cTnT$^{pos}$ cells along the scar endocardium and epicardium, while control animals showed only scattered cTnT$^{pos}$ cells. One explanation is that these cells might have survived the initial hypoxia through increased expression of survival genes. However, this appears very unlikely given the lack of significant differences in the TUNEL analysis. Furthermore, research of β-catenin signaling in apoptosis has shown that stabilization of β-catenin is associated with survival of cardiomyocytes and other cell types, while depletion of β-catenin was found to increase apoptosis (Zelarayan et al., *Cell Cycle* 2007, 6, 2120-2126; Bergmann et al., *Journal of Molecular and Cellular Cardiology* 2004, 37, 681-690). Alternatively, the cells could be derived from surviving cardiomyocytes that, upon hypoxia, dedifferentiate and reenter the cell cycle (Pasumarthi et al., *Circ Res* 2005, 96, 110-118). This hypothesis is not likely since β-catenin depletion did not alter proliferation as quantified by analysis of Sca-1$^{pos}$/Ki67$^{pos}$ cells and in vivo BrdU/Sca-1 or Ki67/Sca-1 double-labeling. Moreover, β-catenin depletion in the early mesoderm decreased proliferation of cardiac precursor cells in the embryonic first heart field (Klaus et al., *Proc Natl Acad Sci USA* 2007, 104:18531-18536). Also, hypertrophy of surviving cardiomyocytes was demonstrated to be unaffected by β-catenin. Thus, none of the cellular mechanisms involving αMHC-dependent gene recombination in adult cardiomyocytes sufficiently explains the phenotype observed here.

Employing the ROSA26 reporter mice in which the expression of the lacZ gene depends on Cre activation, we documented αMHC-dependent gene recombination in cTnT$^{neg}$/Sca-1$^{pos}$ cardiac precursor cells by both immunohistochemistry and flow cytometry techniques. A plausible explanation of this finding could be based on the early embryonic promoter activation of αMHC expression in cardiac mesoderm at E7.5, which gradually decreases to reach a minimal expression at E16 (Lyons et al., *J Cell Biol* 1990, 111, 2427-2436; Sanchez et al., *J Biol Chem* 1991 266, 22419-22426). Similarly, adult cardiac precursors might transiently activate the αMHC promoter during their differentiation towards adult cardiomyocytes. Translocation of Cre recombinase into the nucleus following estrogen induction will result in efficient loxP site recombination. αMHC-dependent Cre expression does not necessarily mean αMHC mRNA and protein expression since this will also depend on post-transcriptional regulatory mechanisms like the recently described Myo-microRNAs network (van Rooij et al., *Science* 2007, 316, 575-579).

In further efforts to substantiate the cardiac lineage of these cells, both flow cytometry and immunohistochemistry were employed. Both techniques confirmed that Sca-1$^{pos}$ cells coexpress the early cardiac specific transcription factor GATA4. In addition to the previously described intra-myocardial niche of cardiac progenitor cells, we identified Sca-1$^{pos}$/β-gal$^{pos}$ cardiac precursor cells in the endo- and epicardial compartment. This resembles the localization of tissue-resident cardiac precursors recently described in zebrafish (Urbanek et al., *Proc Natl Acad Sci USA* 2005, 102, 8692-8697). Similarly, epicardial and endocardial cardiac precursor cells have been identified in mammalian cardiac development (Liebner et al., *J. Cell Biol.* 2004, 166, 359-367 Kruithof et al., *Dev Bio/*2006, 295, 507-522).

Our in vivo and in vitro data suggest that in the adult heart β-catenin depletion enhances differentiation of resident Sca-1$^{pos}$ cells committed to the cardiac lineage. Neither tissue distribution as a measure of cell migration nor proliferation of these cells was altered. The enhanced cardiac differentiation was associated with re-expression of embryonic cardiomyocyte transcription factors Tbx5, Tbx2 and GATA4. Our observation agrees with previous studies suggesting a biphasic role of Wnt/β-catenin pathways during discrete cardiac developmental phases, first positively regulating mesodermal commitment of embryonic stem cells and then playing a negative role during induction and differentiation of cardiac precursor cells (Naito et al., *Proc Natl Aced Sci USA* 2006, 103, 19812-19817 Ueno et al., *Proc Natl Acad Sci USA* 2007, 104, 9685-969). The situation appears to be even more complex as recent studies indicate that two distinct mesodermal populations participate in the formation of the heart. The earliest precursor cell population corresponds to the first heart field and gives rise to the left ventricle; during differentiation Tbx5 expression is specific to the first heart field (FHF). The second cell population marked by the Islet-1 corresponds to the second heart field (SHF) from which right ventricle, atria and outflow tract will arise. Wn/β-catenin signaling regulates self-renewal and expansion of Islet-1 cardiac precursor cells also postnatally. Early mesodermal deletion of β-catenin results in several defects of SHF-derived structures but no major defects were observed in the development of the FHF. Thus, expression of β-catenin might differentially affect the distinct precursor cell populations present in the heart both during cardiac development as well as postnatally.

In sum, it can be reported that β-catenin depletion in adult heart Sca-1$^{pos}$ precursor cells enhances their cardiomyocyte differentiation potential. This was associated with upregulation of Tbx5 expression in vivo, which specifically marks the first heart field, suggesting a re-activation of the left ventricular cell formation gene program. We cannot exclude the participation of other precursor cell population but these changes are sufficient to attenuate LV post-infarct remodeling. Endogenous cardiac regeneration may significantly contribute to adult cardiac remodeling upon stress in addition to previously recognized adult cardiomyocyte apoptosis and hypertrophy.

The invention is further illustrated by the following examples and figures which should not be construed as limiting:

EXAMPLES

Example 1

The β-Catenin Heart-Specific Mouse Models

Figure 1B:
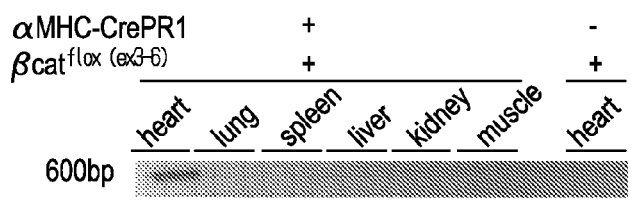
Figure 1C:
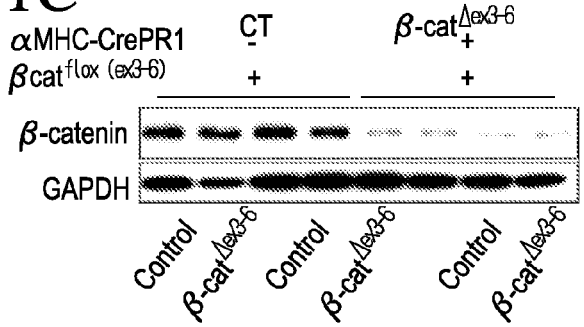
Figure 1D:
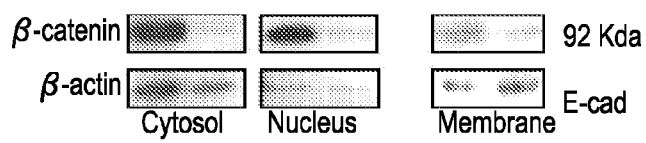
Figure 1E:
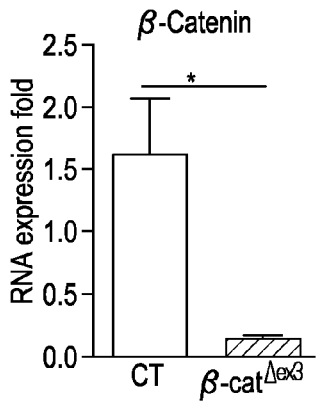

An inducible Cre/loxP system restricting β-catenin depletion to α-MHC positive cells after hormone induction was employed. Recombination efficiency was tested through mating of α-MHC-CrePR1 mice to ROSA 26 reporter mice expressing the lacZ expression cassette under the control of a floxed stop codon. Recombination efficiency after mifepristone injection was determined to be approx. 70% of cardiomyocytes. Induction of Cre recombinase excised exons 3-6 in hearts from β-cat$^{ex3-6\,flox/flox}$×αMHC-CrePR1, resulting in animals that had a heart-specific β-catenin depletion (β-cat$^{\Delta ex3-6}$, FIG. 1B). Successful heart-specific recombination was confirmed by PCR using primers for the recombined DNA that result in a 600 bp fragment (FIG. 1B). No product was obtained from lung, spleen, liver, kidney, or skeletal muscle (FIG. 1B). The downregulation of β-catenin was detected both at the mRNA (FIG. 1E) and protein level analyzing total heart extracts from several mice (FIG. 1C): Active Cre recombinase led to dramatically reduced β-catenin mRNA and protein (FIGS. 1C, D and E). Biochemical methods showed a depletion of β-catenin in all cellular compartments including the nucleus in whole heart tissue extracts. Employing antibodies against both the N- and C-terminus, expression of a truncated β-catenin isoform was excluded as described before (FIGS. 1C and D). In tissue, β-catenin was readily detectable in gap junctions between cardiomyocytes in control hearts, but not in sections from β-catenin heart-depleted mice. Staining of N-cadherin complexing with β-catenin at the cell junction showed no apparent phenotype in β-cat$^{\Delta ex3-6}$ mice with this method (data not shown). Nuclei were stained with DAPI. β-catenin staining was clearly reduced in the mutants while N-cadherin was not affected. Furthermore an enlargement of an area containing a gap junction, which shows the apparent depletion of β-catenin expression was detectable. Electrocardiograms showed no rhythm disturbances in the mice (data not shown).

Figure 2A:
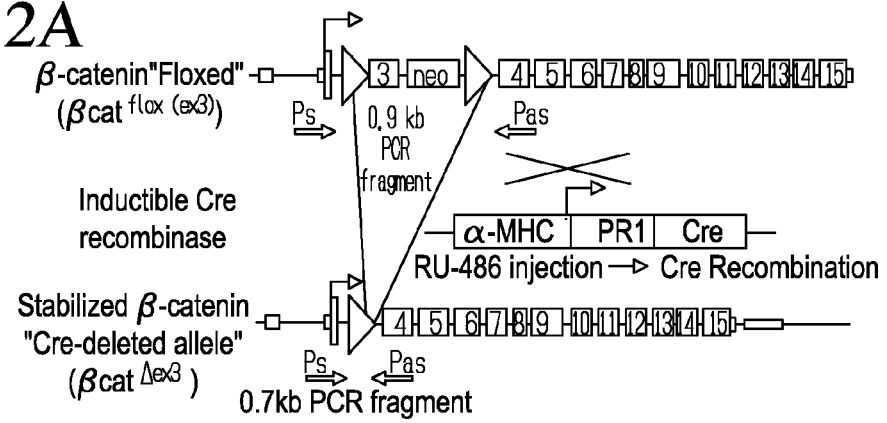
FIG. 2A-D Generation of mice with inducible, heart specific stabilization of β-catenin (β-cat$^{\Delta ex3}$)
Figure 2B:
Figure 2C:
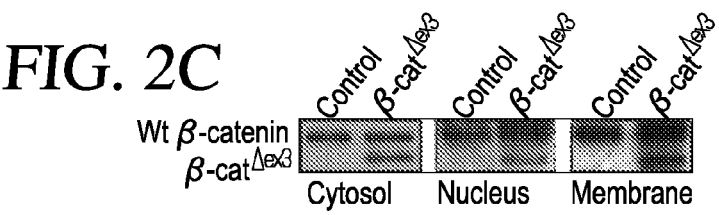

Deletion of exon 3 renders β-catenin to be resistant against GSK3β-induced phosphorylation and consequently blocks proteasom-mediated degradation. Mifepristone administration to β-cat$^{ex3\,flox/flox}$ mice mated to α-MHC-CrePR1 mice generated β-cat$^{\Delta ex3}$ animals (FIG. 2A). Heart-specific Cre recombinase activation excised exon 3 and resulted in mice with heart-restricted, stabilized β-catenin (FIG. 2A). PCR using primers designed to give a 700 bp fragment after successful recombination in contrast to 900 bp beforehand confirmed the genotype (FIG. 2B). Stabilized β-catenin was detectable in cytosolic, membrane and nuclear fractions of whole heart lysates as a smaller band than endogenous β-catenin (FIG. 2C). Staining with N-cadherin, which is complexing with β-catenin at the cell junction, did not reveal an apparent phenotype at the membrane compared to control mice (data not shown). Next, genes regulated transcriptionally by β-catenin were analyzed by real-time PCR with extracts from β-cat$^{\Delta ex3}$ mutants compared to control littermates: Axin2 (7.03±0.7 fold, p<0.001), Tcf-4 (2.92±0.16 fold, p<0.05) and Lef-1 (2.91±0.4 fold, p<0.05) expression was significantly increased (FIG. 2 D). These data prove a functional increase in β-catenin dependent transcription in β-cat$^{\Delta ex3}$ mice as described before concerning other tissues.

Example 2

β-Catenin Depletion Leads to Mild Cardiac Hypertrophy

Figure 3A:
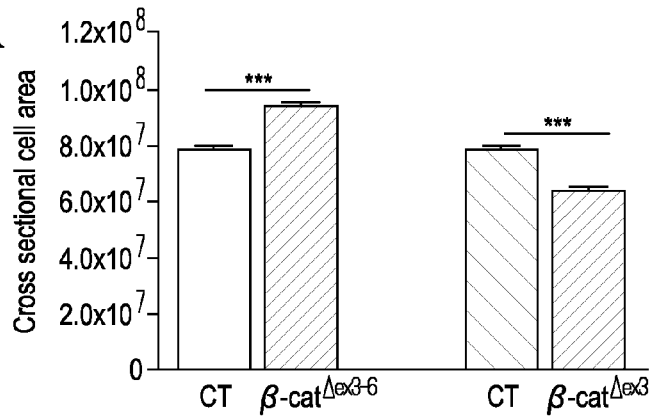
FIG. 3A-C Baseline characterization reveals modest hypertrophy in β-cat$^{\Delta ex3-6}$ and diminished growth in β-cat$^{\Delta ex3}$.
Figure 3B:
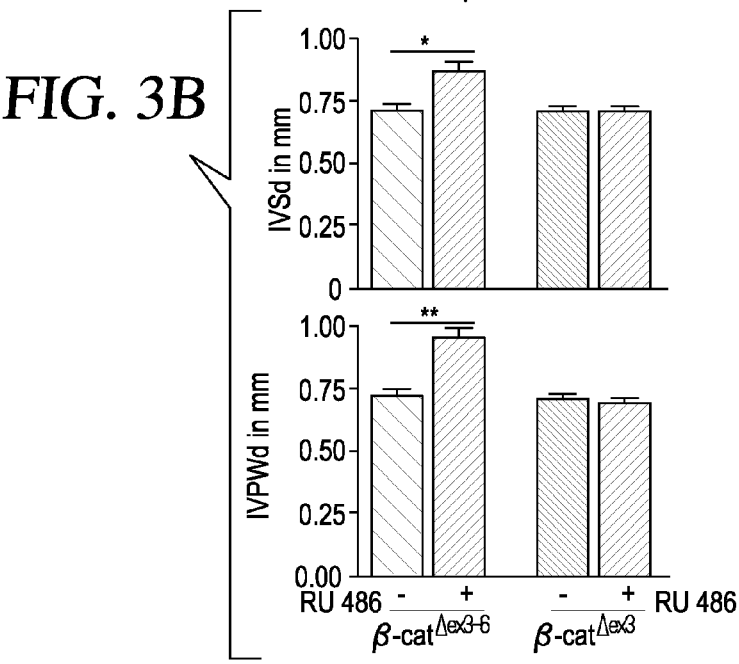
Figure 3C:
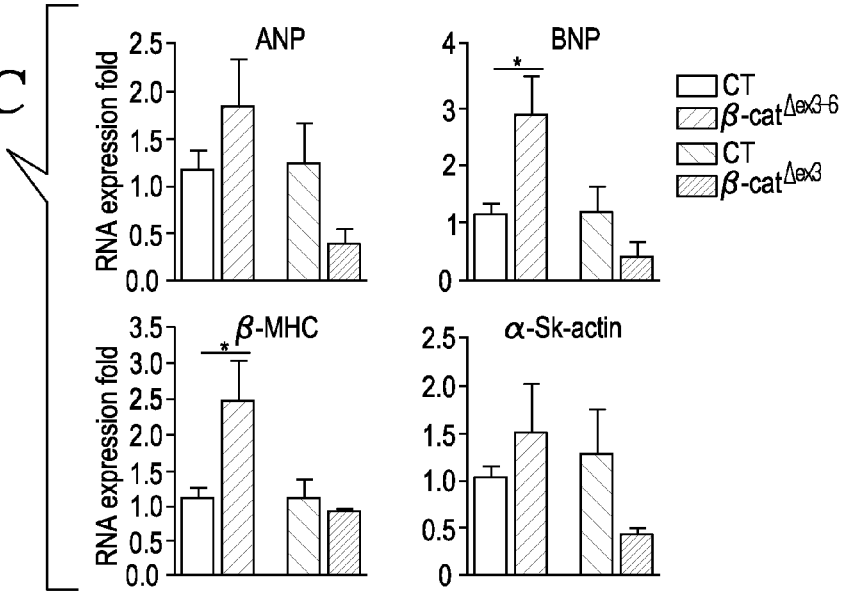

Fourteen days after the final mifepristone injection, the cardiac transverse ventricular cross-sections appeared thicker in β-catenin depleted, compared to wild-type mice (data not shown). Cardiac hypertrophy was confirmed by cross sectional area analysis in vivo: the average cell size from β-catenin depleted mice (9.4×10$^7$±0.14×10$^7$) increased significantly over control cell size (7.9×10$^7$±0.15×10$^7$, P<0.001) (FIG. 3A). Echocardiographic examination demonstrated increased diameters of the diastolic interventricular septum as well as the left ventricular posterior wall (FIG. 3B). No significant changes were seen regarding cavity size or fractional shortening. RNA quantification revealed increased expression of hypertrophy gene markers atrial and brain natriuretic peptides (ANP, BNP), β myosin heavy chain (β-MHC), and α-sarcomeric actin (FIG. 3C). In sum, depletion of β-catenin leads to moderate cardiac hypertrophy in the adult heart. This initial phenotype did not exaggerate and was not accompanied by a loss of cardiac function or any other cardiac deterioration up to the age of 6 months (data not shown).

Example 3

β-Catenin Stabilization Leads to Impaired Cardiac Growth

Deletion of the endogenous exon 3 results in a single copy gene of stabilized β-catenin under the control of the endogenous reporter. In contrast to our initial hypothesis based on previously published in vitro and in vivo data, β-catenin stabilization (β-cat$^{\Delta ex3}$) did not cause hypertrophy (FIG. 3). In fact, when cross-sectional area was calculated 14 days after Cre recombinase induction by mifepristone, a significantly decreased cell size was observed (CT 7.8×10$^7$±1.1×10$^6$ vs β-cat$^{\Delta ex3}$ 6.4×10$^7$±1.4×10$^6$ p<0.001, FIG. 3A). Cells from stabilized β-catenin mice were approximately 82% the size of control cells. Hypertrophy gene marker expression was the inverse of the β-catenin depletion experiment. Hypertrophic markers were either stable (β-MHC) or downregulated in the β-cat$^{\Delta ex3}$ samples compared to controls (FIG. 3C). Over six months, the animals developed and behaved normally. Taken together, the above data suggest that depleting β-catenin in the adult heart results in adaptive cardiac hypertrophy, while expression of a non-degradable mutant results in a phenotype of smaller cardiomyocytes indicating impaired cardiac growth or cardiac muscular atrophy.

Example 4

Responses to AngII in the β-Catenin Mouse Models

Figure 4A:
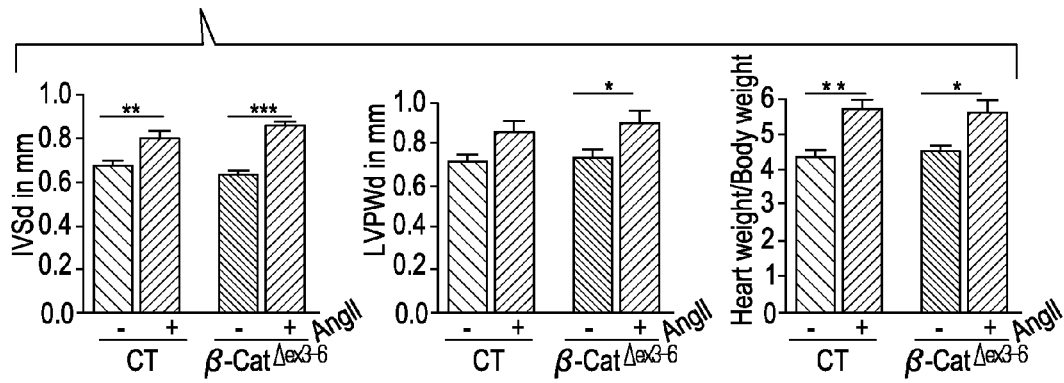
FIG. 4A-C AngII stimulation induces hypertrophy in both control and β-catenin depleted mice.
Figure 4B:
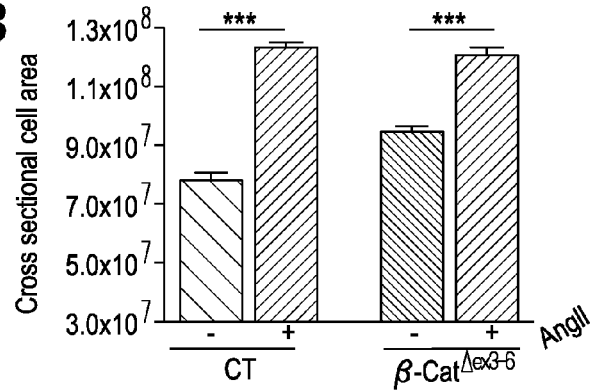
Figure 4C:
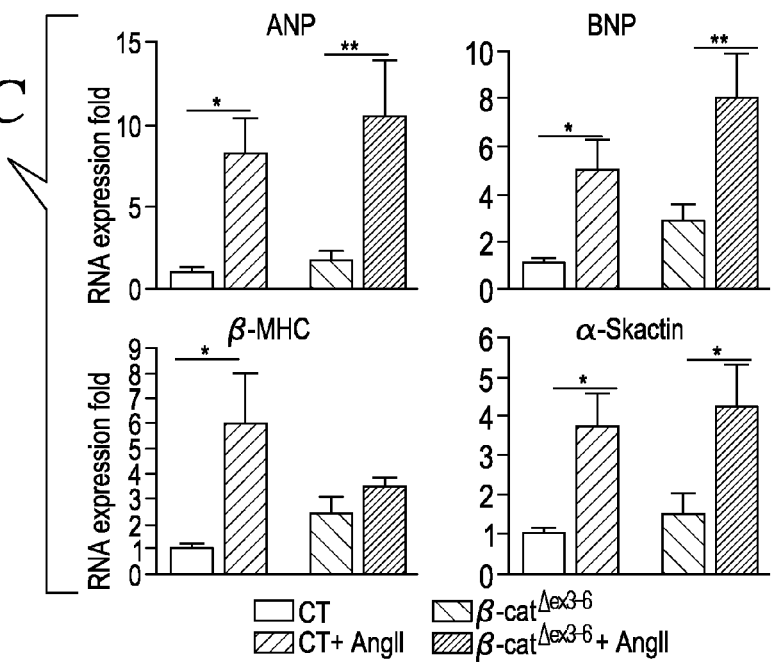

After 12 days' AngII infusion at pressure doses (1.4 μg Kg$^{-1}$ min$^{-1}$), control animals developed hypertrophy as judged by echocardiography, gene regulation, in vivo cross sectional area, and heart/body weight ratio as described before (FIG. 4). From the M-mode echocardiography imaging, a thickened inter-ventricular septum and LV posterior wall after AngII was identified in control animals (FIG. 4A). Even if at baseline β-catenin depleted mice exhibited an increase of the cardiomycyte area (data not shown), treatment with AngII further enhanced cellular cross sectional area (12.1×10$^7$±0.24×10$^7$ a.u.) to absolute values similar to control mice (12.3×10$^7$±0.19×10$^7$ a.u.) (FIG. 4B). LV wall thickening was identical in β-catenin heart-depleted animals and control littermates after AngII (data not shown). Heart weights normalized to body weight showed a significant increase for both control and β-catenin depletion mice (FIG. 4A, suppl. table 1). Moreover, AngII increased gene expression of several hypertrophy gene markers in both control and b-catenin heart-depleted animals with the exception of β-myosin heavy chain (FIG. 4 C). A lack of β-MHC upregulation in response to stress stimuli might be indicative of adaptive cardiac remodeling preserving LV-function as described before (van Rooij E et al., *Circ Res.* 2004; 94:18e-26).

Figure 5A:
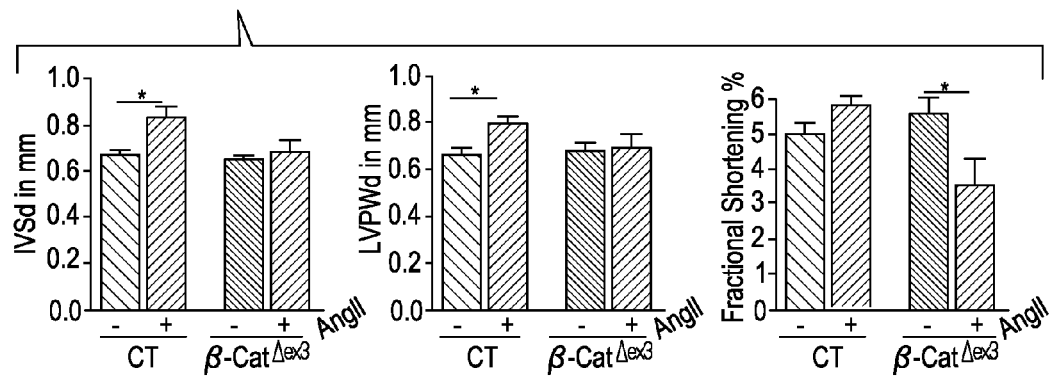
FIG. 5A-C β-catenin stabilization attenuates AngII-induced cardiac hypertrophy but leads to decreased cardiac function.
Figure 5B:
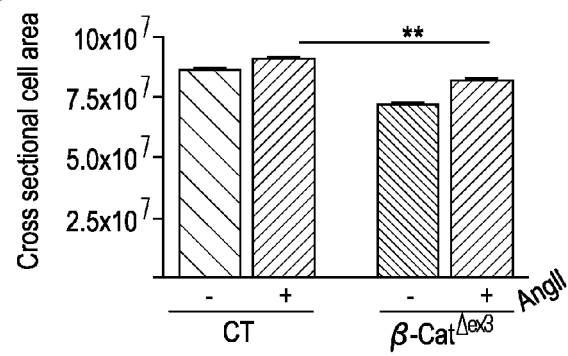

The effects of 12 days' AngII infusion in mice with cardiac stabilized β-catenin (β-cat$^{\Delta ex3}$) were opposite in kind to those of mice with β-catenin heart-depletion. Echocardiography showed no significant change in the wall thickness following AngII treatment in β-catenin stabilized mice in contrast to control littermates, where wall thickness increased significantly (data not shown). ANP (β-cat$^{\Delta ex3}$ 0.4±0.15; β-cat$^{\Delta ex3}$+AngII 1.03±0.15; p<0.01) and BNP (β-cat$^{\Delta ex3}$ 0.43±0.24; β-cat$^{\Delta ex3}$+AngII 1.4±0.27; p<0.01) expression was induced by AngII but final values were generally lower than in control mice (ANP: CT+AngII 2.3±0.8; BNP: CT+AngII 2.6±0.6). In vivo, cardiomyocyte size following AngII treatment significantly increased over baseline in both models, but was significantly smaller in β-cat$^{\Delta ex3}$ compared to control animals treated with AngII (CT 9.07×10$^7$±0.14×10$^7$ vs β-cat$^{\Delta ex3}$ 8.14×10$^7$±0.14×10$^7$, P<0.001; FIG. 5B).

Figure 5C:
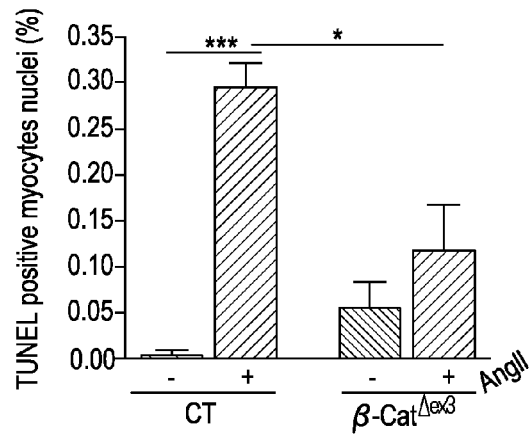

As expected, fractional shortening increased in control mice after AngII treatment (31.1±1.6% to 36.2±1.6%). However, β-catenin heart-stabilization led to reduced fractional shortening after AngII infusion (34.7±2.9% to 22.4±4.5%, p<0.05). These absolute values in animals aged 10 to 14 weeks are identical to a serial analysis of the age-dependant changes employing the same high-resolution echo techniques as used for these studies. The reduced fractional shortening in β-catenin stabilized mice was not due to increased cardiomyocyte apoptosis as β-catenin stabilized mice demonstrated rather fewer TUNEL/α-sarcomeric actin/DAPI-positive cells after AngII treatment compared to controls (β-cat$^{\Delta ex3}$: 0.058±0.027% at baseline to 0.120±0.049% after AngII; p<0.001 compared to CT+AngII 0.297±0.025%; FIG. 5C). In contrast, analysis of mice with β-catenin depletion showed a non-significant increase of TUNEL-positive cells at baseline with similar results after AngII treatment (CT: 0.004±0.004; β-cat$^{\Delta ex\ 3-6}$: 0.112±0.044%; after AngII: CT 0.09±0.02%; β-cat$^{\Delta ex3-6}$: 0.2±0.13%). These absolute values are similar to other reports, i.e. rates of apoptotic cardiomyocytes after trans-aortic constriction. Moreover, no significant differences concerning fibrosis occurring focally throughout the LV wall was observed when both transgenic models were to their respective controls. In sum, AngII induced hypertrophy is not affected by β-catenin depletion, while mice with stabilized β-catenin exhibit an impaired hypertrophic response to AngII. Apoptosis-related mechanisms do not explain these findings.

Example 5

Analysis of Cardiac β-Catenin Target Genes

Figure 2D:
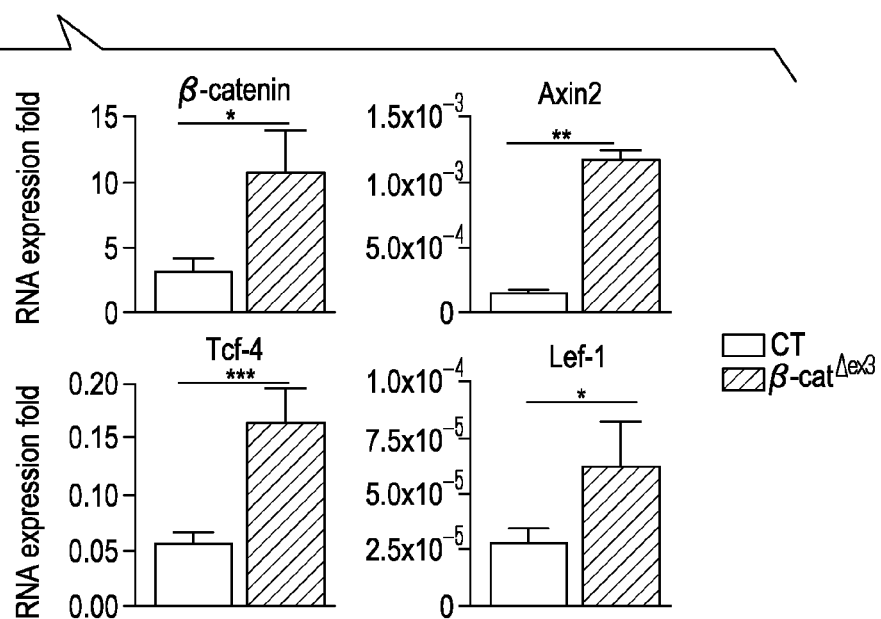
Figure 6A:
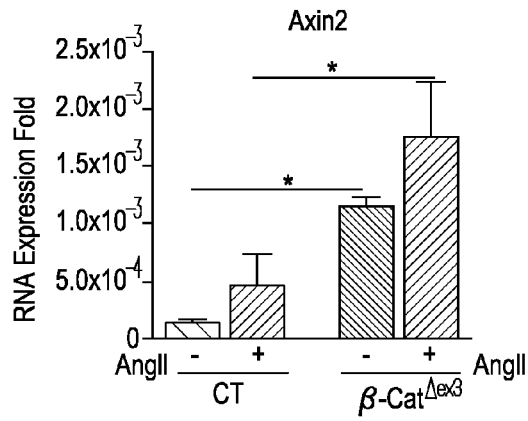
FIG. 6A-E Gene regulation in β-cat$^{\Delta ex3}$ mice.
Figure 6B:
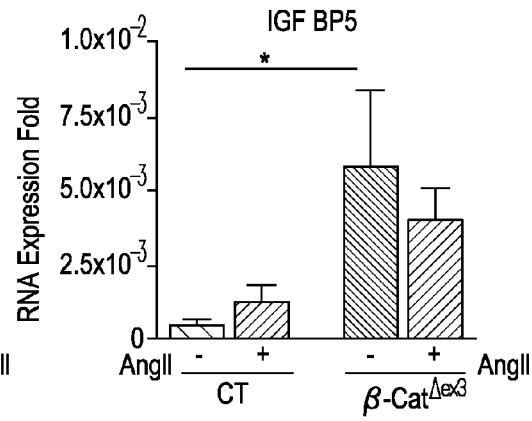

Next, several target genes were analyzed which have previously been described to be regulated in a β-catenin-dependent fashion either in embryonic development (GATA-4, Nkx 2.5, MEF2a, Tbx5 and Tbx20) or in the context of chronic PI3-kinase/AKT signaling (atrogin 1, IGFBP5) (Skurk et al. J. Biol. Chem. 2005; 280:20814-20823). Analysis was performed in whole heart RNA extracts. GATA-4, Nkx2.5, MEF2a and atrogin 1 expression was not significantly altered by AngII treatment or α-MHC-dependent changes in β-catenin levels. Axin2 levels were increased by AngII in both control and β-catenin stabilized mice, although the baseline levels were already significantly increased in β-cat$^{\Delta ex3}$ mice (FIG. 6A, FIG. 2D).

Interestingly, β-catenin levels affected gene expression of IGFBP5, a protein inhibitory for the IGF-signaling cascade. IGFBP5 was found upregulated in hearts with genetically mediated chronic AKT activation (Skurk et al. J. Biol. Chem. 2005; 280:20814-20823). Functionally, IGFBP5 is implicated in muscle atrophy. Here, IGFBP5 was upregulated in β-cat$^{\Delta ex3}$ mice relative to control littermates (9.02±3.2 fold). No significant change of expression levels were observed upon AngII stimulation.

Figure 6C:
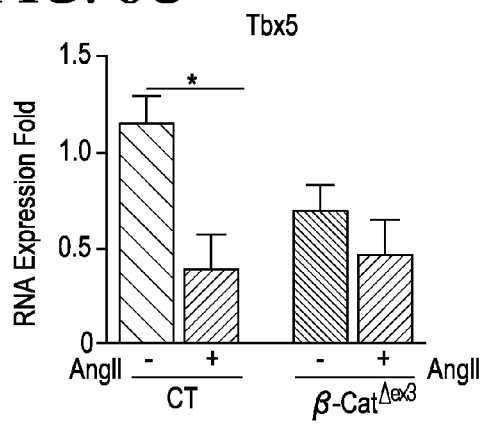
Figure 6D:
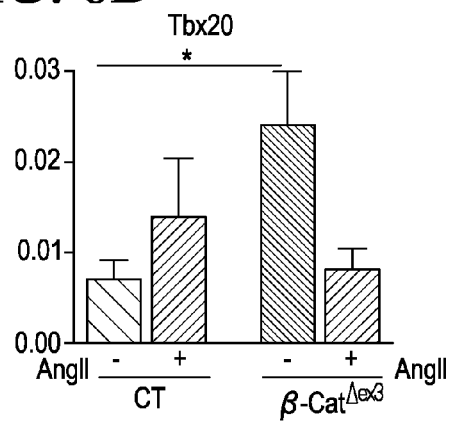
Figure 6E:
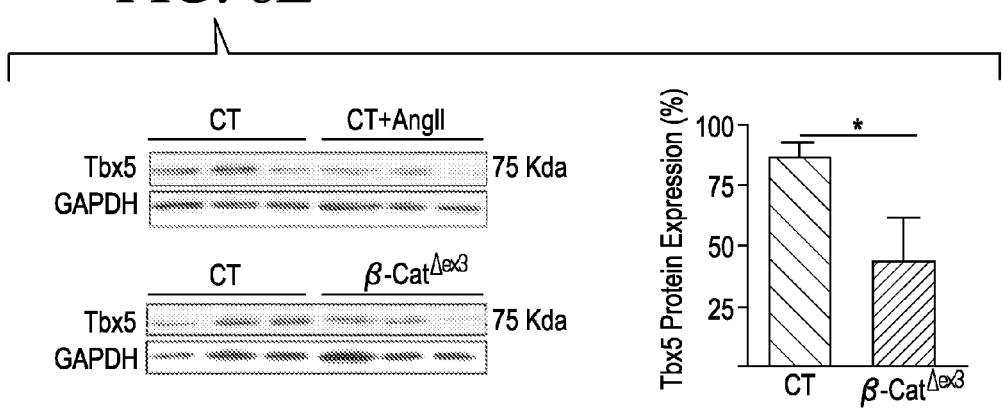

At baseline, β-catenin stabilization led to reduced Tbx5 mRNA and protein levels while Tbx20 mRNA was found to be upregulated (FIG. 6C+D; Tbx20 vs. control: 3.3±0.31 fold, p<0.05). AngII treatment significantly downregulated Tbx5 gene expression in control mice; this effect was lost in the β-catenin stabilized mice (FIG. 6 C). No significant effect of AngII on Tbx20 gene expression was observed (FIG. 6C). These results suggest differential regulation of T-box proteins downstream of β-catenin in association with a phenotype of impaired cardiac growth and performance.

Example 6

Figure 7A:
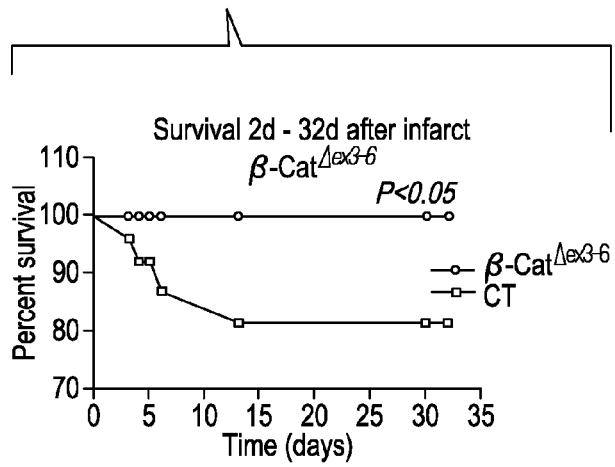
FIGS. 7A, B Kaplan-Meier survival analysis.
Figure 7B:
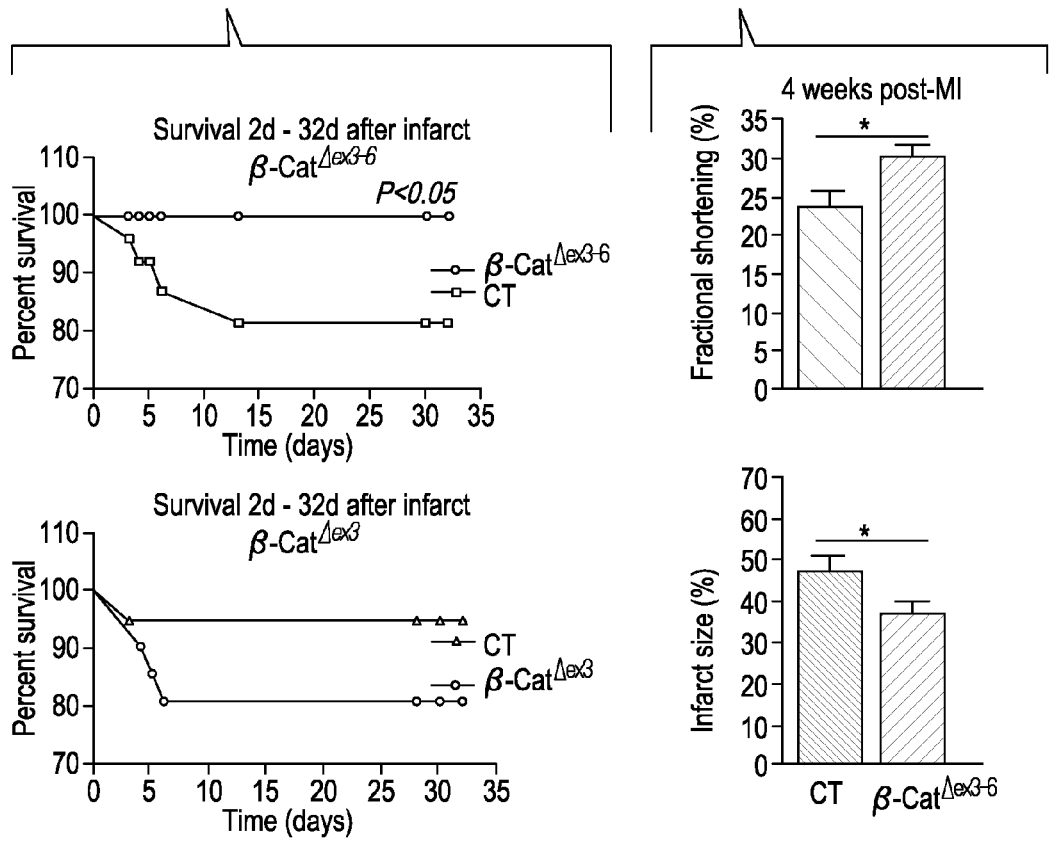

6-Catenin Depletion Attenuates Left Ventricular Remodeling after Myocardial Infarction Beta-catenin depletion significantly decreased mortality over the first four weeks after experimental myocardial infarction (CT n=11, β-catΔex3-6 n=15*P<0.05), while β-catenin stabilized mice showed a non-significant increase of mortality (FIG. 7A). β-catenin depleted (β-catΔex3-6), stabilized (β-catΔex3), and respective control littermates were subjected to chronic ligation of the left anterior descendent coronary artery (LAD). To our surprise, β-catenin depleted animals exhibited improved fractional shortening (β-catΔex3-6: 30.2±1.6% vs CT: 24.0±1.9%; CT: n=7; 6-catΔex3-6: n=13*P<0.05) (FIG. 7 B, Top). Heart weight/body weight ratio was reduced upon β-catenin depletion (control: 6.1±0.42; 6-catΔex3-6: 5.3±0.21, data not shown). In addition, infarct size measured in Masson Trichome stained heart sections was significantly reduced in β-catenin depleted mice at four weeks in comparison to controls (β-catΔex3-6: 37.2±2.1% vs CT: 47.2±3.7%; CT: n=6, β-catΔex3-6: n=6*P<0.05) (bottom, FIG. 7 B). Mice with β-catenin stabilization displayed no major differences compared to control littermates in infarct size or LV function as measured by echocardiography (data not shown). A different cellularity of the scar upon β-catenin depletion in β-catΔex3-6 mice was observed by immunofluorescent staining for cardiac Troponin T (cTnT)pos cells. A prominent endocardial and epicardial layer of cTnTpos cardiomyocytes was detected upon 6-catenin depletion, while controls showed a fibrotic scar with only few cTnTpos cells (data not shown). Similarly, β-catenin stabilized mice (β-catΔex3) and their respective control mice showed only few cTnTpos cells in the scar (data not shown). In sum, depletion of β-catenin in αMHCpos cardiac cells attenuates ischemic LV-remodeling and postinfarct mortality.

In this or a closely related experimental set-up, β-catenin depletion could also been shown to lead to reduced mRNA expression of heart failure markers ANP and BNP at two weeks (CT$^{\Delta ex3-6}$n=5; 6-cat$^{\Delta ex3-6}$n=15).

Example 7

In Vitro Differentiation Assay of β-Catenin Depleted Cells

In order to prove that the observed improvement of cardiac function following experimental infarct is due to enhanced cardiac regeneration from endogenous precursor cells upon β-catenin depletion, sca-1$^{pos}$ cardiac precursor cells were isolated. Highly enriched (>95% purity) cardiac sca-1$^{pos}$ precursor cells were subjected to an in vitro differentiation assay. Cell preparations were generated by to two rounds of magnetic selection.

Primary cultures of neonatal mouse cardiomyocytes employed for co-culture differentiation were prepared by enzymatic digestion of ventricles obtained from 1-3-day-old FVB mice. Before co-culture, Sca-1+ cells were labeled with the CM-Dil cell tracer (Molecular Probes). After 10 days, co-cultures were fixed with 4% paraformaldehyde and analyzed by α-sarcomeric-actinin/CM-Dil/DAPI immunofluorescence co-staining. The number of double α-sarcomeric actin/CM-Dir$^{pos}$ cells was calculated in relation to the total CM-Dir$^{pos}$ cells.

Figure 8:
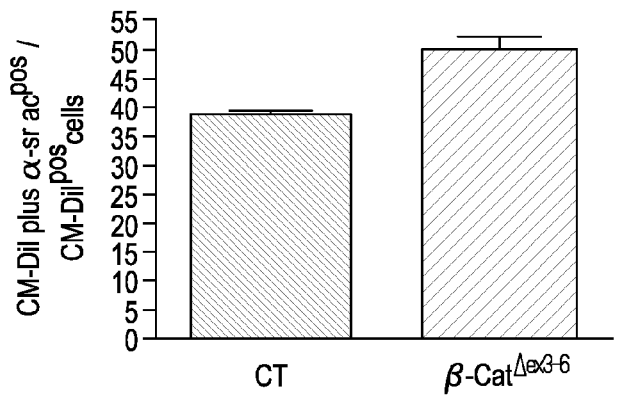
FIG. 8 In vitro differentiation assay.

As shown in FIG. 8, Sca-1 cells isolated from β-cat$^{\Delta ex3-6}$ mice indeed showed significantly increased differentiation capacity in comparison to cells isolated from their control littermates (controls (n=10): 38±1.0% of α-sarcomeric actinin$^{pos}$+CM-DiL$^{pos}$/total CM-Dil$^{pos}$; β-cat$^{\Delta ex3-6}$ (n=10): 49.9±2.4%, p<0.001).

Example 8

Inhibition of β-Catenin by KLF15

Figure 9A:
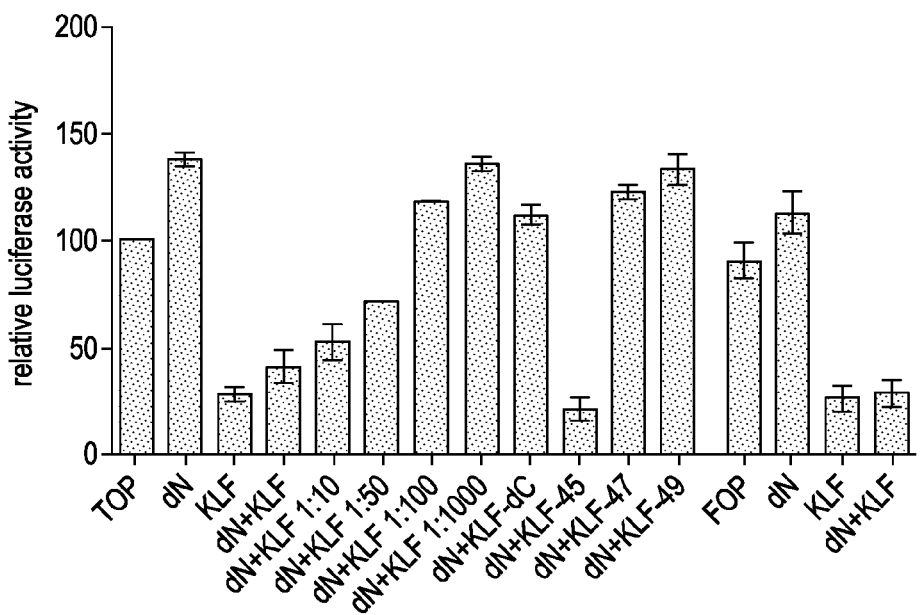
FIGS. 9A, B Inhibition of β-catenin-dependent gene transcription by KLF15.
Figure 9B:
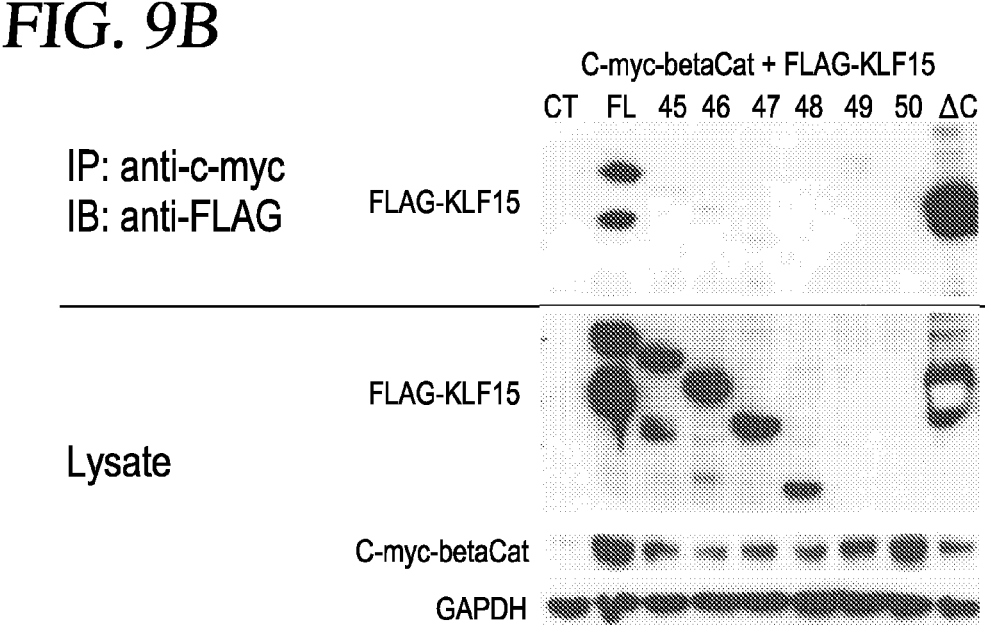

The transcription factor Krüppel-like factor (KLF) 15 inhibits β-catenin dependent transcription in isolated cardiomyocytes through a direct interaction of its C-terminal end as shown by topflash reporter gene assay and immunoprecipitation assays (FIG. 9 A). Isolated neonatal rat cardiomyocytes were used as a model system to analyze factors inhibiting β-catenin dependent gene regulation. β-catenin dependent transcription was measured by reporter gene assay. KLF15 was found to inhibit topflash reporter gene activation dose dependendly. Concerning the molecular mechanisms, KLF15 mutants were analyzed concerning their direct protein interaction to β-catenin employing immunoprecipitation analysis (FIG. 9 B). The interacting domain was mapped to the N-terminus between amino acids 1 and 45 (FIG. 9 B), where as the C-terminus was also required for the transcriptional repressive function. Given the previously demonstrated beneficial effect of β-catenin depletion on cardiac remodeling, any peptide of substance mimicking the effect of KLF15 on β-catenin function or any derivative thereof is expected to be beneficial in cardiac remodeling.

Example 9

Improved Cardiac Function Upon β-Catenin Depletion is not Associated with Changes in Adult Cardiomyocyte Hypertrophy or Apoptosis As a molecular and cellular mechanism of attenuated LV remodeling upon β-catenin depletion, it was hypothesized that adult cardiomyocyte hypertrophy and/or apoptosis was altered. Hypertrophy and apoptosis was investigated 2 and 4 weeks after LAD ligation. No significant difference with respect to the hypertrophy markers α-skeletal-actin and β-MHC between β-cat$^{\Delta ex3-6}$ mice and their controls 2 weeks after LAD was found (data not shown). At 4 weeks, neither gene markers of cardiomyocyte hypertrophy nor echocardiographic septal or free wall thickness as a measure of global LV hypertrophy showed any significant differences (data not shown). Because hypertrophy of the noninfarcted myocardium contributes to LV remodeling (Virag J A et al. 2007, Am J Pathol 171:1431-1440), myofiber area was measured in the remote zone. No significant change was detected in β-cat$^{\Delta ex3-6}$ mice (data not shown) or β-cat$^{\Delta ex3}$ mice (data not shown) compared to their control littermates both at 2 and 4 weeks after infarct. In addition, we found no evidence for an altered rate of cardiomyocyte apoptosis as detected by TUNEL assay (data not shown). Therefore, it was concluded that the attenuation of cardiac remodeling after ischemia upon β-catenin depletion is not mediated by inhibition of cardiac hypertrophy and/or decreased apoptosis of adult cardiomyocytes.

Example 10

Figure 10A:
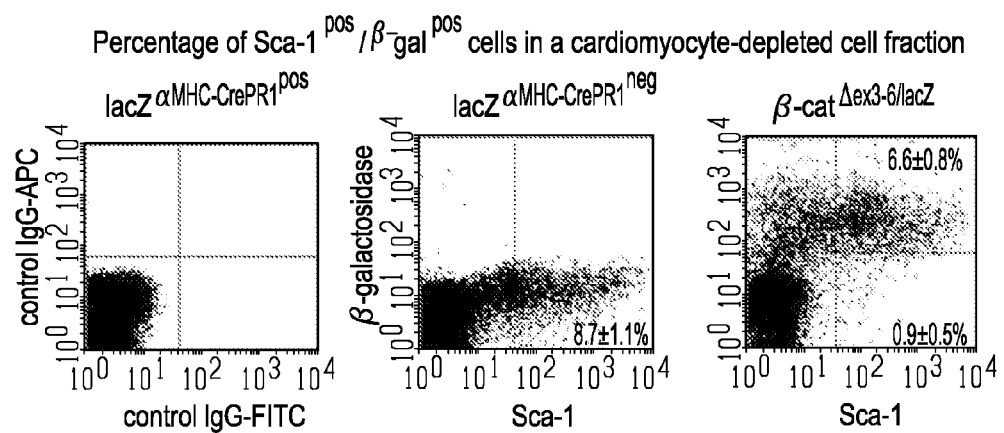
FIG. 10A-E Activation of the αMHC-promoter in cardiac progenitor cells.
Figure 10B:
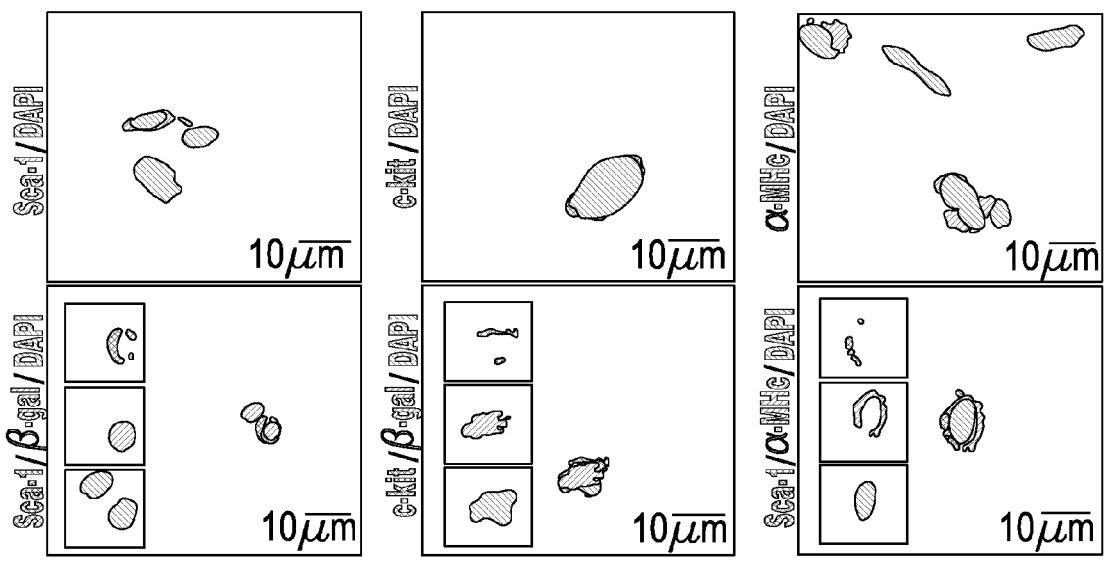

Resident Cardiac Progenitor Cells are Targeted by αMHC-Dependent Gene Recombination Since neither adult cardiomyocyte apoptosis nor hypertrophy explained the observed phenotype, the question was posed whether other cardiac cell types, apart from mature cardiomyocytes, were affected by αMHC-dependent gene recombination. The ROSA26 reporter mice allowed for the identification of cells targeted for Cre recombination through detection of β-gal expression. The aim was to identify β-gal$^{pos}$ cells using flow cytometry in a cardiomyocyte-depleted cell fraction from adult heart and found were ~10% β-gal$^{pos}$ cells. Next, it was tested whether the β-gal$^{pos}$ cells have stem cell characteristics and the coexpression of the cardiac progenitor cell marker Sca-1 was analyzed. Of the noncardiomyocyte cells, 8.8±0.4% were detected to be Sca-1$^{pos}$ (data not shown). More than 80% of these Sca-1$^{pos}$ cells (6.6±0.8% cells of the total noncardiomyocyte cell population) were β-gal$^{pos}$ in both CT$^{\Delta ex3-6/lacZ}$ and β-cat$^{\Delta ex3-6/lacZ}$. lacZ$^{\alpha MHC-Cre-neg}$ littermate mice were used as negative controls for β-gal detection (FIG. 10A and data not shown). Similarly, flow cytometry analysis of another heart-specific inducible Cre line, the αMHC-MerCreMer mice (Sohal D S et al. 2001, Circ Res 89:20-25) mated to the ROSA26 reporter mice showed >60% of the Sca-1$^{pos}$ cells to coexpress β-gal following Cre-induction (data not shown). Immunofluorescence analysis of the noncardiomyocyte cell fraction proved coexpression of the Sca-1 and c-kit epitope in a subpopulation of β-gal$^{pos}$ cells. Moreover, αMHC protein expression was observed in a subpopulation of Sca-1$^{pos}$ cells confirming the activation of the endogenous αMHC promoter and protein expression in the identified cell population (FIG. 10B).

Figure 10C:
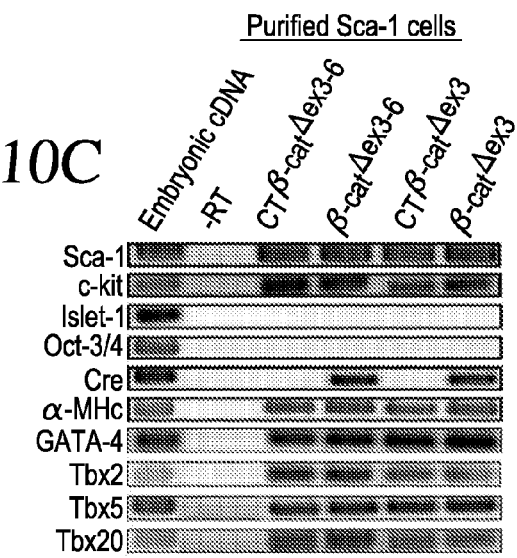

Using magnetic cell sorting (MACS) technology cardiac Sca-1$^{pos}$ cells were enriched from β-catenin depleted, stabilized and their respective control littermates to >95% for further characterization. Independent from the genotypes, mRNA quantification showed coexpression of c-kit. Other known precursor cell markers such as Islet-1 or Oct3/4 were not coexpressed, suggesting different subsets of cardiac precursor cells to be present in the adult heart. Sca-1$^{pos}$ cells from β-cat$^{\Delta ex3-6}$ and β-cat$^{\Delta ex3}$ showed both Cre recombinase and αMHC gene expression consistent with activation of the αMHC promoter in these cells (FIG. 10C). Gene expression of the cardiac transcription factors GATA4, Tbx2, Tbx5, and Tbx20 was detected, confirming that these Sca-1$^{pos}$/β-gal$^{pos}$ cells in the noncardiomyocyte fraction are progenitor cells of the cardiac lineage (FIG. 10C and data not shown).

Figure 10D:
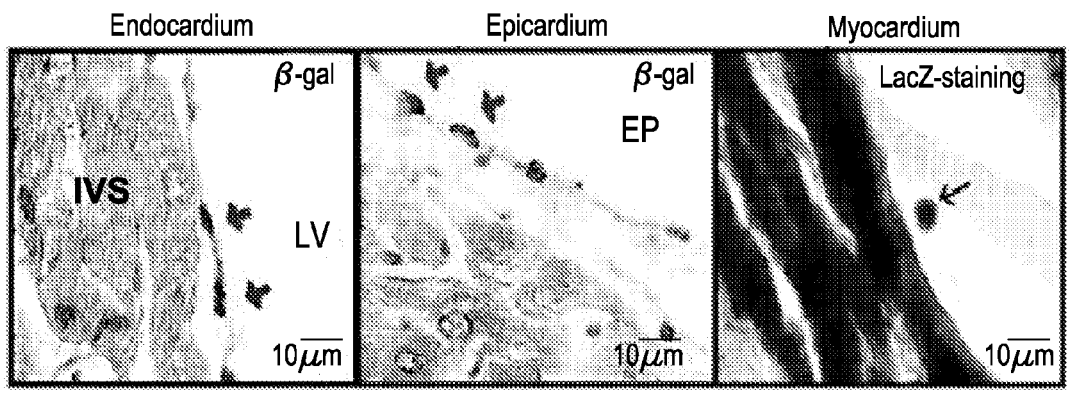
Figure 10E:
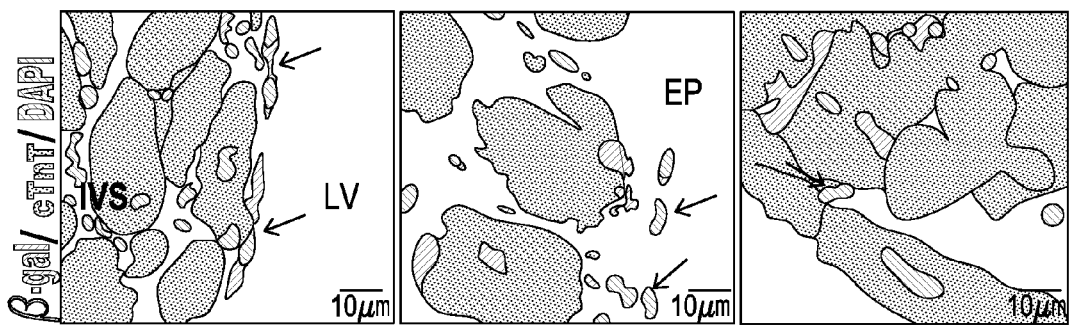

Aiming to visualize the identified cardiac progenitor cells in vivo, heart sections from β-cat$^{\Delta ex3-6/lacZ}$ and CT$^{\Delta ex3-6/lacZ}$ mice at baseline were analyzed. Small intramyocardial β-gal-expressing cells were detected by enzymatic lacZ reaction. In addition, immunoperoxidase detection identified endo- and epicardial β-gal$^{pos}$ cells (arrows, FIG. 10D). Heart sections costained with β-gal and cTnT showed a subendo- and subepicardial layer of β-gal$^{pos}$/cTnT$^{neg}$ cells with a large nucleus to cytoplasmic ratio as expected for cardiac precursor cells (FIG. 10E and data not shown). Double stainings of consecutives slides confirmed β-gal$^{pos}$/Sca-1$^{pos}$ cells to be cTnT$^{neg}$, GATA4$^{pos}$, and Tbx5$^{pos}$ (data not shown). Thus, a population of αMHC$^{pos}$/Sca-1$^{pos}$/c-kit$^{pos}$/GATA4$^{pos}$/cTnT$^{neg}$ cardiac progenitor cells were identified in an endocardial and epicardial compartment.

Example 11

Cardiac Progenitor Cell Proliferation and Distribution Following Experimental Infarct It was demonstrated that αMHC$^{pos}$/Sca-1$^{pos}$/cTnT$^{neg}$ cardiac precursor cells are targeted for β-catenin depletion. As a hallmark of cardiac precursor cells, a BrdU/Sca-1 and Sca-1$^{pos}$/Ki67$^{pos}$ double staining identified proliferating Sca-1$^{pos}$ cells. β-Catenin depletion did not affect the number of proliferating Sca-1$^{pos}$ cells (11A and data not shown). While these data provide evidence for self-renewal of cardiac resident Sca-1$^{pos}$ precursor cells no evidence was found that differences in proliferation rate explains the observed functional phenotype upon β-catenin depletion.

Figure 11A:
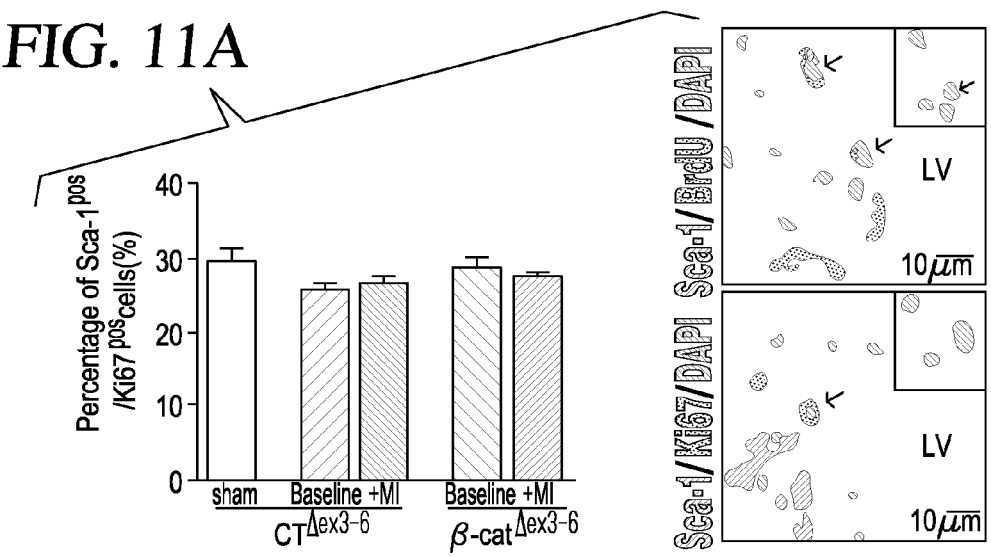
FIG. 11A-C Proliferation and tissue distribution of β-gal$^{pos}$/GATA4$^{pos}$/cTnT$^{neg}$ cardiac progenitor cells after myocardial infarct.
Figure 11B:
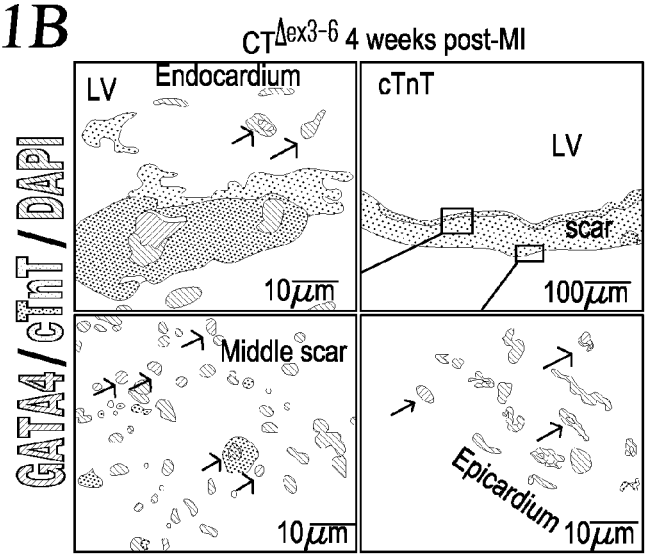
Figure 11C:
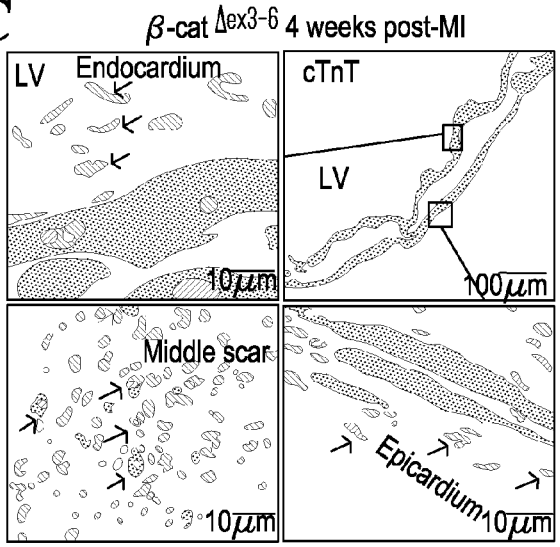

Next, the question was posed whether altered migration might contribute to LV remodeling upon β-catenin depletion. The distribution of Sca-1$^{pos}$/GATA4$^{pos}$/cTnT$^{neg}$ cardiac progenitor cells was investigated using confocal microscopy in heart sections 2 and 4 weeks after ischemia. At 2 weeks the distribution of β-gal$^{pos}$/Sca-1$^{pos}$/GATA4$^{pos}$/CTnT$^{neg}$ progenitor cells and a semiquantification of the Sca-1 cells in the scar vs. remote zone showed no major difference between β-cat$^{Δex3-6}$ and controls (data not shown). A prominent layer of GATA4$^{pos}$/cTnT$^{neg}$ cells was detected along the scar at 4 weeks (white arrows in FIGS. 11B and C). Additionally, a few small GATA4$^{pos}$/cTnT$^{pos}$ cells were localized in the ischemic region of β-cat$^{Δex3-6}$ and control littermates in the proximity (subendo- and subepicardium) of the compartment where the Sca-1$^{pos}$/β-gal$^{pos}$ cardiac precursor cells were observed initially (endo- and epicardium) (darker arrows in FIGS. 11B and C). In sum, no evidence was found that altered migration of cardiac progenitor cells would explain the observed functional phenotype or the more prominent layer of cTnT$^{pos}$ cells in the scar of β-cat$^{Δex3-6}$ mice.

Figure 12D:
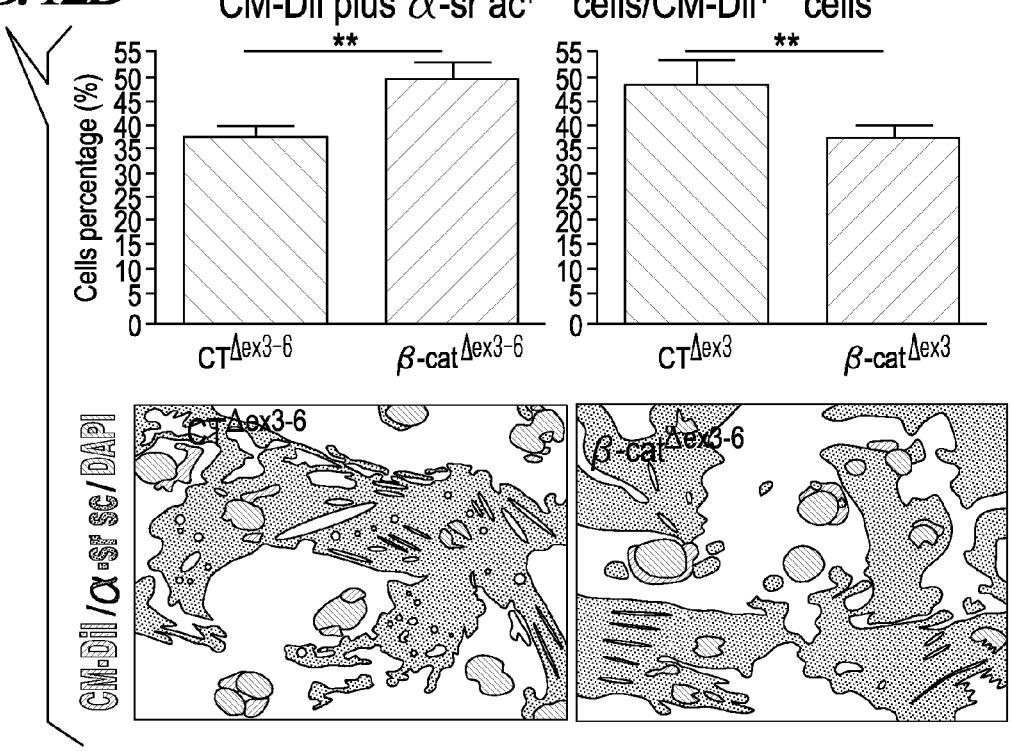

Example 12

β-Catenin Depletion Enhances Cardiac Progenitor Cell Differentiation After Ischemia The next question that was posed was whether depleting β-catenin alters differentiation of cardiac-resident progenitor cells toward cTnT$^{pos}$ cardiomyocytes. Flow cytometry analysis of the noncardiomyocyte cell fraction revealed the fraction of Sca-1$^{pos}$ cells coexpressing GATA4 to significantly increase in β-cat$^{Δex3-6}$ mice 4 weeks after infarct compared to β-cat$^{Δex3-6}$ mice at baseline and control mice after infarct (FIG. 12A and data not shown). This increased expression of cardiac differentiation markers was accompanied by a decrease of total Sca-1$^{pos}$ cells in β-cat$^{Δex3-6}$ mice vs. baseline. Control animals did not decrease the Sca-1$^{pos}$ cell population after infarct (FIG. 12B).

If progenitor cell differentiation contributes to stabilize the scar, early cTnT$^{pos}$-expressing cells with smaller cell size than mature cardiomyocytes should be detectable. Therefore, we analyzed the scar cellularity 4 weeks after ischemia. β-Catenin-depleted mice showed a significant increase of GATA4$^{pos}$/cTnT$^{pos}$ cells (white circle in FIG. 12C) with <16 μm² surface area (matched to DAPI$^{pos}$ cell number). In contrast, mice with stabilized β-catenin did not show any significant difference in comparison to their respective controls (FIG. 12C).

Figure 12E:
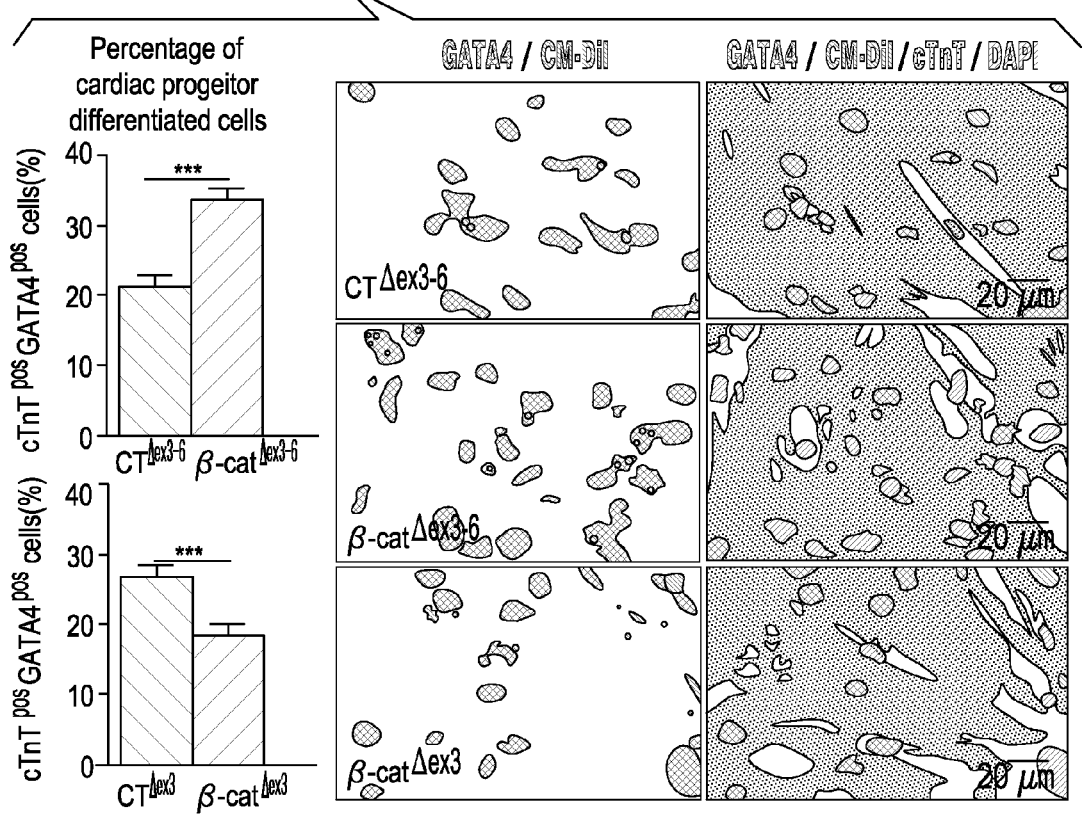

To confirm the hypothesis of enhanced precursor cell differentiation upon β-catenin depletion, an in vitro differentiation assay was performed. Isolated Sca-1 cells from β-catenin depleted, stabilized, and respective control littermates were enriched by MACS to >95% purity and labeled with the cell tracer CM-DiI. The cells were cocultured with neonatal mouse (FVB WT strain) cardiomyocytes for 10 days and the number of double α-sarcomeric actin (α-sr ac)$^{pos}$/CM-DiI$^{pos}$ cells was calculated in relation to the total CM-DiI$^{pos}$ cells. Sca-1$^{pos}$ cells isolated from β-cat$^{Δex3-6}$ mice showed significantly increased differentiation capacity in comparison to cells isolated from controls (CT$^{Δex3-6}$n=10: 38±1.0% of α-sr ac$^{pos}$+CM-DiI$^{pos}$/total CM-DiI$^{pos}$; β-cat$^{Δex3-6}$ n=10: 49.9±2.4% , P<0.001, FIG. 12D). Similar to the in vivo situation, we detected an increased percentage of differentiated GATA4$^{pos}$/cTnT$^{pos}$ cells in β-catenin-depleted cells compared to control cells (CT$^{Δex3-6}$:21.2±1.5% vs. β-cat$^{Δex3-6}$: 34.0±1.6% , P<0.001, FIG. 12E). In contrast, Sca-1$^{pos}$ cells isolated from β-catenin-stabilized mice exhibited decreased differentiation capacity (CT$^{Δex3}$n=4: 49.1%±4.8 of α-sr ac$^{pos}$+CM-DiI$^{pos}$/total CM-DiI$^{pos}$; β-cat$^{Δex3}$n=6: 38.3±2.1% *, P<0.05, FIG. 4D) and decreased differentiated GATA4$^{pos}$/cTnT$^{pos}$ cells (CT$^{Δex3}$: 26.7±0.9% vs. β-cat$^{Δex3}$: 18.3±0.7% **, P<0.001, FIG. 12E). Collectively, these data indicate that following chronic LAD ligation, β-catenin depletion enhances resident endogenous Sca-1$^{pos}$ cardiac progenitor cell differentiation toward GATA4$^{pos}$/cTnT$^{pos}$/α-sr ac$^{pos}$-expressing cells (scheme in FIG. 12G). Enhancing endogenous repair mechanisms contributes to global LV remodeling including infarct size extension (Virag J A et al., (2007), *Am J Pathol* 171:1431-1440).

Example 13

Figure 12F:
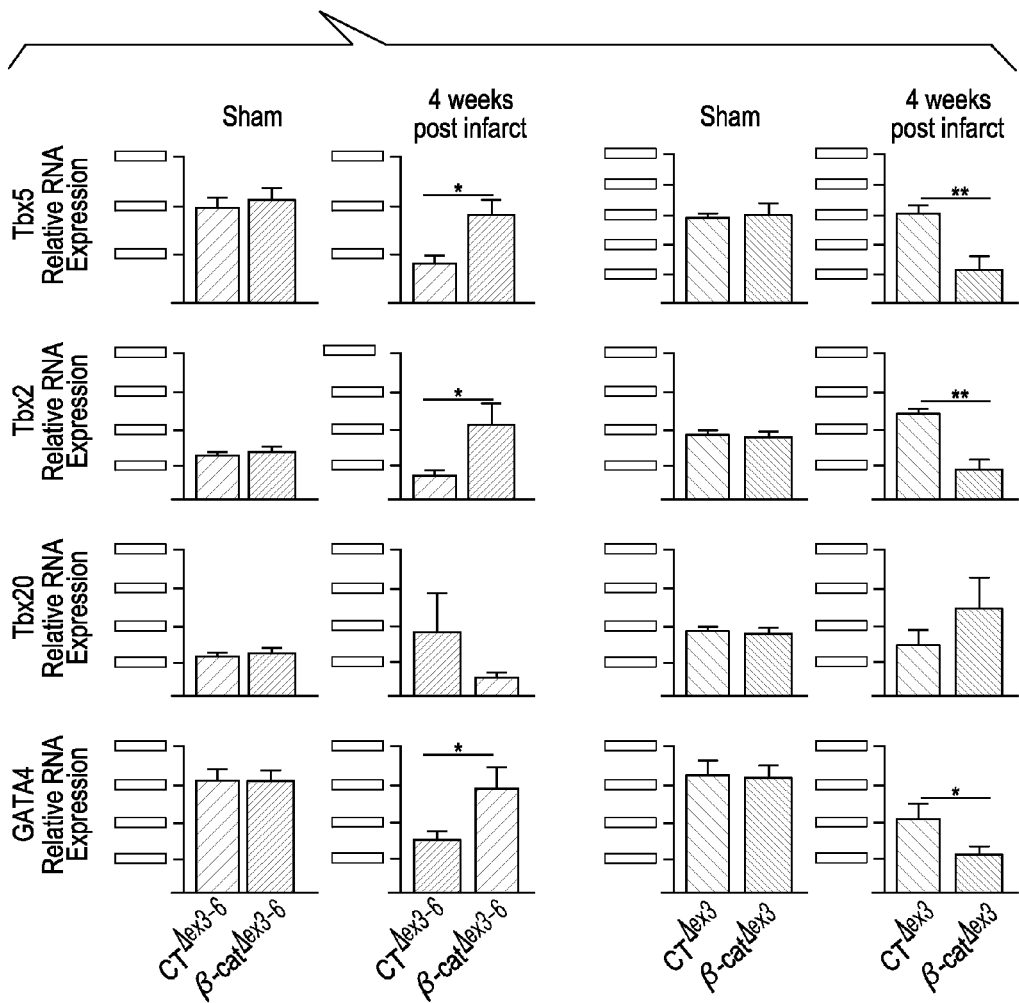
Figure 12G:
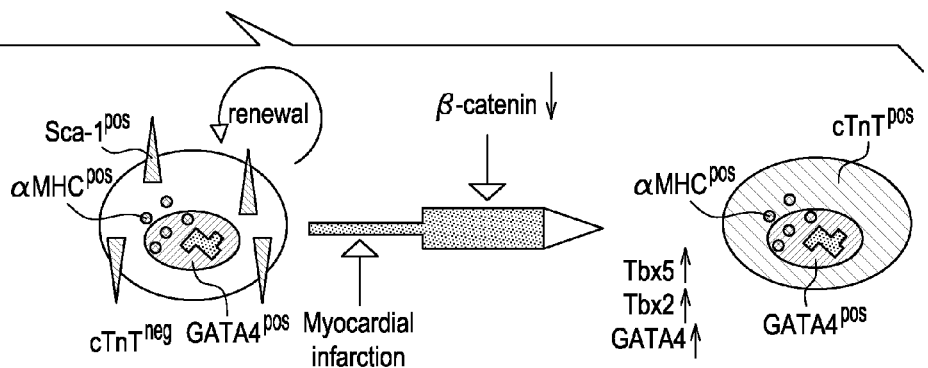

Re-expression of Cardiac Developmental Transcription Factors in Ischemic Adult Heart During embryogenesis, the cardiac mesoderm activates several transcriptional regulators of the cardiac program including GATA4 and members of the T-box family necessary for ventricular cardiac differentiation in response to inductive signals (Mori A D et al., (2006), *Dev Biol* 297:566-586). Tbx5 is specifically expressed in the first heart field, which gives rise to left ventricular cardiomyocytes (Bruneau B G et al., (1999), *Dev Biol* 211:100-108). Therefore, Tbx5 and GATA4 expression was studied following infarct via quantitative real-time PCR using heart samples obtained from the apex containing scar tissue, border zone, and remote area. Four weeks after infarct, expression of Tbx2, Tbx5, and GATA4 was significantly upregulated in β-cat$^{Δex3-6}$ mice in comparison to controls and Tbx20 was downregulated. Gene regulation in heart samples from mice with β-catenin stabilization showed the opposite results (FIG. 12F). These data suggest β-catenin depletion in the adult myocardium to induce cardiomyocyte differentiation similar to the embryonic formation of the left ventricle.

DETAILED DESCRIPTION OF THE DRAWINGS

FIG. 1:
(A) Representative mating scheme between mice carrying β-catenin floxed exons 3-6 and αMHC-CrePR1 mice. Mice have been described previously. For heart-specific, progesterone inducible Cre recombinase expression αMHC-CrePR1 mice were employed. In β-cat$^{ex3-6\ flox/flox}$×α-MHC-CrePR1, administration of mifepristone leads to loxP site recombination with the appearance of a 600 bp band (B). Hybridization sites of the primers are indicated. (C) Western blot (WB) from whole heart lysate of both control and β-cat$^{Δex3-6}$ mice. A significant reduction of β-catenin protein expression in β-cat$^{Δex3-6}$ is detected by a C-terminal binding antibody. (D) A second WB employing a N-terminal binding antibody indicates diminished expression of β-catenin in all cellular compartments (cytosol, nucleus and membrane). β-actin was used as control for cytosol and nucleus and E-cadherin for membrane. (E) Also at the mRNA level, β-catenin quantification by Real Time PCR normalized to GAPDH revealed decreased expression of full length β-catenin cDNA (right panel).

FIG. 2:
(A) The scheme depicts the mating between α-MHC-CrePR1 mice and β-cat$^{ex3\ flox/flox}$, which upon recombination lack the GSK 3β phosphorylation site resulting in organ-specific stabilization of β-catenin. (B) Genomic PCR analysis shows the truncated β-catenin product (700 bp) following specific recombination in the heart of in β-cat$^{Δex3}$ mice; hybridization sites of the primers are indicated. (C) Western blot depicting expression of the truncated form of β-catenin protein in β-cat$^{Δex3}$ mice in different cellular compartments (cytosol, nucleus and membrane). (D) β-catenin target genes Axin2, Tcf-4 and Lef-1 are upregulated in β-cat$^{\Delta ex3}$ total heart RNA extracts as measured by real time PCR. Fold expression is relative to GAPDH calculated as copy numbers.

FIG. 3:

A quantification of transverse sections of control, β-cat$^{\Delta ex3-6}$ and β-cat$^{\Delta ex3}$ hearts is shown. Cross sectional area analysis by Wheat germ agglutinin (WGA)-FITC staining demonstrates modest cardiac hypertrophy in mice with cardiac-specific β-catenin depletion (β-cat$^{\Delta ex3-6}$) as well as diminished growth after β-catenin stabilization (β-cat$^{\Delta ex3}$). n=8-11 mice per group. (B) Echocardiographic diastolic diameters of inter-ventricular septum (IVSd) and left ventricular posterior wall (LVPWd) demonstrate cardiac hypertrophy after β-catenin depletion. No significant change in wall dimensions after β-catenin stabilization was observed (n≥15 for each group). (C) RNA quantification by real time RT-PCR analysis of hypertrophic markers after β-catenin depletion and stabilization. *=P<0.05, **=P<0.01; expression fold is relative to GAPDH control.

FIG. 4:

(A) Both control and β-catenin depleted β-cat$^{\Delta ex3-6}$ mice exhibit cardiac hypertrophy after 14 days of microosmotic minipump infusion of AngII (1.4 µg/kg$^{-1}$/min$^{-1}$). Representative examples of M-mode echocardiograms (not shown), quantification of echocardiographic parameters and heart/body weight from control and β-cat$^{\Delta ex3-6}$ mice with and without AngII infusion are shown (n≥6 for each group) (B) Myocyte cross-sectional area increases in both control and β-catenin depleted β-cat$^{\Delta ex3-6}$ mice as measured by WGA-FITC staining of cardiac tissue sections and quantification from control or β-cat$^{\Delta ex3-6}$ mice with AngII infusion (data not shown). At least 500 cells were measured for each animal, n≥4 mice per group. (C) Significant upregulation of ANP, BNP and α-sarcomeric actin normalized to GAPDH after AngII in control and β-catenin depleted β-cat$^{\Delta ex3-6}$ mice. Quantification by real-time PCR of whole heart RNA samples from control (white) or β-cat$^{\Delta ex3-6}$ (grey) mice without (open bars) and with (shaded bars) AngII infusion. *=P<0.05, =P<0.01, *=P<0.001.

FIG. 5:

(A) Attenuation of cardiac hypertrophy after AngII in β-catenin stabilized mice is accompanied by significant deterioration of systolic function as measured by fractional shortening (right bar graph). Representative examples of M-mode echocardiograms and quantification from control or β-cat$^{\Delta ex3}$ mice with and without AngII infusion. Quantification of echocardiographic wall size and fractional shortening from control or β-cat$^{\Delta ex3}$ mice with and without AngII infusion. *=P<0.05, =P<0.01. (B) Increase of myocyte cross-sectional area after AngII is attenuated in β-catenin stabilized β-cat$^{\Delta ex3}$ mice (data not shown). At least 400 cells counted per animal, mice per group. *=P<0.001. (C) Rates of TUNEL/α-sarcomeric actin/DAPI-positive cardiomyocytes after AngII infusion decrease after β-catenin stabilization in β-cat$^{\Delta ex3}$. In addition to the TUNEL-assay, slides were co-stained with α-sarcomeric actin and DAPI in control mice and β-cat$^{\Delta ex3}$ mice before and after AngII stimulation (data not shown).

FIG. 6:

RNA normalized to GAPDH levels in whole heart extracts as measured by Real Time PCR in β-catenin stabilized mice (β-cat$^{\Delta ex3}$). (A) Up-regulation of β-catenin target gene Axin 2 by AngII treatment in β-cat$^{\Delta ex3}$ compared to control animals. (B) Upregulation of Insulin like—Growth Factor Binding Protein 5 (IGFBP5) was found by RT-PCR at baseline in the β-cat$^{\Delta ex3}$ mice in comparison to controls, while no significant change was observed by AngII stimulation. (C) T-box protein 5 (Tbx5) and (D) T-box protein 20 (Tbx20) mRNA levels are differentially regulated in β-cat$^{\Delta ex3}$ mice upon AngII stimulation. (E) Tbx5 Western blot showing the down-regulation of its expression in control mice after AngII treatment (upper panel) as well as in β-cat$^{\Delta ex3}$ mice at baseline (lower panel). WB quantification was done by densitometry normalized to GAPDH (right panel).

FIG. 7:

A: Kaplan-Meier survival curve of mice with comparable infarct size. Top: Significantly enhanced survival was observed in β-catenin depleted β-catΔex3-6 mice four weeks after experimental infarct (left bar graph, *P<0.05, CT: n=11; β-catΔex3-6: n=15). Bottom: In contrast, increased mortality was observed in β-catenin stabilized β-cat$^{\Delta ex3}$ mice compared to control animals (right bar graph, CT: n=7; 8-cat$^{\Delta ex3}$: n=7). Scale bars: 100 µm. MI: myocardial infarct, LV: Left ventricle, cTnT: cardiac Troponin T.

B: Top: β-catenin depletion in β-cat$^{\Delta ex3-6}$ mice results in improved fractional shortening (top: *P<0.05, CT: n=7; β-cat$^{\Delta ex3-6}$: n=13) and reduced infarct size (bottom: *P<0.05, CT: n=6; β-catΔex3-6: n=6) four weeks after infarct.

FIG. 8:

A co-culture differentiation assay demonstrates significantly increased differentiation of isolated Sca-1 pos precursor cells towards α-sarcomeric-actininpos cardiomyocytes from β-catenin depleted β-catΔex3-6 mice compared to isolated Sca-1 cells from control mice. (CT: n=10; β-catΔex3-6: n=10; **: p<0.001).

FIG. 9:

Inhibition of β-catenin-dependent gene transcription by KLF15. (A) Reporter gene assay in isolated neonatal cardiomyocytes showing activation of the topflash reporter gene by stabilized β-catenin (ΔN-catenin; dN). A dose-dependent inhibition is observed by co-transfection of KLF15. (B) Co-immunoprecipitation assays demonstrate interaction of only the full length and C-terminally deleted KLF15, but not the mutants with N-terminal deletions.

FIG. 10:

Activation of the αMHC-promoter in cardiac progenitor cells.

(A) Flow cytometry analysis reveals >80% of the noncardiomyocytes to coexpress β-gal and Sca-1 at baseline. Cre$^{neg}$ mice were used as negative control. IgG-rabbit-APC and IgG-FITC antibodies were used as a control to discard unspecific staining. (B) Representative immunofluorescence picture of β-gal$^{pos}$ cells from the cardiomyocyte depleted cell fraction proving coexpression of the Sca-1 and c-kit epitope. A subpopulation of cells coexpresses αMHC and Sca-1. (C) Analysis of Sca-1 cells gene expression by quantitative real-time PCR documenting expression of αMHC, c-kit, and cardiac transcription markers (GATA4, Tbx5). (D and E) Immunohistochemistry of adult heart from lacZ$^{\alpha MHC-Cre}$ mice. Activation of the αMHC promoter was analyzed by β-gal reporter gene expression. Small cells, with a high nuclei/cytoplasm ratio, positive for β-gal were detected by immunoperoxidase, enzymatic lacZ detection, and fluorescence staining in endo-, epi-, and myocardium.

FIG. 11:

Proliferation and tissue distribution of β-gal$^{pos}$/GATA4$^{pos}$/cTnT$^{neg}$ cardiac progenitor cells after myocardial infarct.

(A) Quantification of Sca-1$^{pos}$/Ki67$^{pos}$ cell proliferation in a cardiomyocyte-depleted cell fraction by flow cytometry shows no significant differences between CT$^{\Delta ex3-6}$ and β-cat$^{\Delta ex3-6}$ mice neither at baseline nor after ischemia. Immunofluorescence shows colocalization of Sca-1$^{pos}$/BrdU$^{pos}$ and Sca-1$^{pos}$/Ki67$^{pos}$ cells 2 weeks after infarct proving the proliferative capacity of these cells. (B and C) β-Catenin depleted β-cat$^{\Delta ex3-6}$ mice exhibit a layer of cTnT$^{pos}$ cardiomyocytes along the scar, which appears less prominent in control mice (B and C, Upper Right). The subendocardial and subepicardial layer of the infarct scar is populated with small GATA4$^{pos}$/cTnT$^{neg}$ cells (white arrows). In addition, small GATA4$^{pos}$/cTnT$^{pos}$ cells are detected within the scar area of both β-cat$^{\Delta ex3-6}$ and control mice (grey arrows in B and C, Lower Left). No significant difference in tissue distribution is detected. LV, left ventricle; MI, myocardial infarct.

FIG. 12:

β-Catenin depletion enhances cardiomyocyte differentiation of Sca-1$^{pos}$ precursor cells following experimental infarct.

(A) Significant increase of the Sca-1$^{pos}$/GATA4$^{pos}$ cell fraction in β-cat$^{\Delta ex3-6}$ mice 4 weeks after infarct vs. baseline and sham mice, which is not observed in CT$^{\Delta ex3-6}$ animals. It was accompanied by a nonsignificant decrease of total Sca1$^{pos}$ cells in β-cat$^{\Delta ex3-6}$ mice while control mice tend to upregulate the total Sca-1 cells (B). (C) In Vivo quantification of GATA4$^{pos}$/cTnT$^{pos}$ cells in the scar with a cell area<16 μm$^2$ shows a significant increase of these cells in β-cat$^{\Delta ex3-6}$ mice compared to controls. A representative confocal image is shown (white circles). (D) In Vitro increased differentiation of isolated Sca-1$^{pos}$ cells toward α-sr ac$^{pos}$ cardiomyocytes from β-cat$^{\Delta ex3-6}$ mice compared to isolated Sca-1 cells from CT$^{\Delta ex3-6}$ mice. The opposite effect was observed in β-catenin-stabilized mice. A representative picture of a 10-day CM-Dil-labeled coculture stained with α-sr ac is shown. (E) Similarly, in vitro differentiation of isolated Sca-1 cells toward GATA4$^{pos}$/cTnT$^{pos}$ cells increases in β-cat$^{\Delta ex3-6}$ compared to cells from CT$^{\Delta ex3-6}$ mice. The same cell population is decreased in β-cat$^{\Delta ex3}$ mice. (F) Quantitative real-time PCR of heart samples 4 weeks after infarct shows an increased expression of markers for ventricular cardiomyocyte differentiation Tbx5, Tbx2, and GATA4 in β-cat$^{\Delta ex3-6}$ mice compared to CT$^{\Delta ex3-6}$. Reciprocal regulation was observed in β-cat$^{\Delta ex3}$ mice in comparison to CT$^{\Delta ex3}$ mice. (G) Hypothetical scheme of αMHC$^{pos}$ cardiac precursor cells differentiation in vivo triggered by ischemia and amplified by β-catenin depletion. *, P<0.05; **, P<0.001.

DISCUSSION

The above experiments demonstrate, among others, a resident cardiac progenitor cell population exhibiting αMHC-promoter activity and expression of cardiac transcription factors GATA4 and Tbx5 as specific markers for the first heart field (FHF) giving rise to the left ventricle during embryonic cardiac development. Enhancing signaling cascades orchestrating LV embryonic cardiomyocyte differentiation, namely depletion of β-catenin, positively affects global LV function and survival at 4 weeks. Enhanced cardiomyocyte differentiation of endogenous cardiac resident stem cells are suggested to mediate this effect by limiting secondary infarct expansion.

β-Catenin Depletion Attenuates Postischemic Mortality.

Infarct mortality was ameliorated by β-catenin depletion already during the first 2 weeks post infarct. Similarly, ubiquitous overexpression of the Wnt signaling antagonist frizzledA, which prevents β-catenin accumulation after infarct, resulted in reduced mortality between 2 and 5 days after permanent LAD ligation because of reduced cardiac rupture (Barandon L, et al., (2003) *Circulation* 108:2282-2289). Fatal arrhythmias resulting from "vulnerable" myocardium might be reduced through the effects of β-catenin on cellular scar composition. In association with the improved LV function following infarct, we found an increased number of cTnT$^{pos}$-expressing cells with small cell size upon β-catenin depletion.

These data suggest that despite the dramatic size difference between the small-identified cTnT$^{pos}$ cells in the scar and the adult cardiomyocytes, these cells might positively affect secondary scar expansion (Beltrami A P et al. 2003, *Cell* 114: 763-776) and therefore affect ventricular wall stability early on.

Cardiomyocyte Hypertrophy and Apoptosis Upon β-Catenin Depletion.

Four weeks after chronic LAD ligation mice with β-catenin depletion exhibited a complete lining of cTnT$^{pos}$ cells along the scar subendocardium and subepicardium, while control animals showed only scattered cTnT$^{pos}$ cells. One explanation is that these cells might have survived the initial hypoxia through increased expression of survival genes. However, we have not observed significant differences in the TUNEL analysis. A second explanation is that β-catenin influences proliferation but β-catenin depletion did not alter proliferation as quantified by analysis of Sca-1$^{pos}$/Ki67$^{pos}$ cells. Accordingly, β-catenin depletion in the early mesoderm decreased proliferation of cardiac precursor cells in the embryonic FHF (Klaus A et al., (2007) *Proc Natl Acad Sci USA* 104:18531-18536). Upregulation of β-catenin enhances expansion of Islet-1 cardiac stem cells (Qyang Y, et al. 2007, *Cell Stem Cell* 1:165-179; Cohen E D et al. 2007, *J Clin Invest* 117:1794-1804). Lastly, hypertrophy of surviving cardiomyocytes was demonstrated to be unaffected upon β-catenin depletion. Thus, none of the cellular mechanisms involving αMHC-dependent gene recombination in adult cardiomyocytes sufficiently explains the phenotype observed here.

Identification of αMHC$^{pos}$ Cardiac Resident Precursor Cells.

Employing the ROSA26 reporter mice in which the expression of the lacZ gene depends on Cre activation, we documented αMHC-dependent gene recombination, mRNA, and protein expression in a cTnT$^{neg}$ cell population. Cardiac stem cells were previously shown to express αMHC during early cardiac developmental stages in embryoid bodies in vitro (Doss M X et al., 2007, *Genome Biol* 8:992). As the adult cardiac cell population under investigation here expresses markers of cell proliferation (Ki67, BrdU) and cardiomyocyte lineage markers (GATA4, Tbx5) it fulfills the criteria of a cardiac endogenous precursor cell. It overlaps in part with the Sca-1 and c-kit positive cardiac stem cell population; however, the cells are negative for Islet-1 and Oct3/4.

Two distinct mesodermal populations participate in the formation of the heart. The earliest progenitor cell population corresponds to the FHF, which expresses Tbx5 during differentiation and gives rise to the LV (Bruneau B G et al. 1999, *Dev Biol* 211:100-108). The second population identified by Islet-1 expression corresponds to the second heart field (SHF) from which right ventricle, atria, and outflow tract will arise (Klaus A et al. 2007, *Proc Natl Acad Sci USA* 104:18531-18536; Lin L et al., 2007, *Proc Natl Acad Sci USA* 104:9313-9318; Kwon C et al. 2007, *Proc Natl Acad Sci USA* 104: 10894-10899; Urbanek K et al. 2005, *Proc Natl Acad Sci USA* 102:8692-8697). The above findings of the coexpression of αMHC and specific cardiac transcription factors like GATA4, and Tbx5 characteristic for the LV, suggest the existence of an αMHC$^{pos}$/cTnT$^{neg}$ cardiac committed FHF stem cell population in the adult heart.

β-Catenin Downregulation Improves Cardiac Function After Experimental Infarct.

As described above, a subpopulation of cardiac resident progenitors committed to the cardiac lineage to be targeted for β-catenin depletion, which results in enhanced differentiation. Similar observations have been described for Islet-1$^{pos}$ cardiac precursors: differentiation decreased upon β-catenin stabilization while proliferation of the undifferentiated cells is enhanced (Qyang Y et al. 2007, *Cell Stem Cell* 1:165-179). Moreover, upregulation of Tbx5 and GATA4 gene expression was observed after ischemia, suggesting a reactivation of the LV cell differentiation program in adult heart in adaptation to injury.

The findings support that endogenous cardiac regeneration contributes to LV remodeling following chronic ischemia through differentiation of resident precursor cells, amplified by β-catenin downregulation. Similarly, increased differentiation of Sca-1$^{pos}$ resident cardiac precursor cells was observed upon upregulation of FGF2. Depletion of FGF2 was found to worsen LV remodeling by enhancing secondary infarct expansion (Qyang Y et al 2007, *Stem Cell* 1:165-179; Naito A T et al. 2006, *Proc. Natl Acad Sci USA* 103: 19812-19817, Ueno S et al. 2007, *Proc. Natl Acad Sci USA* 104: 9685-9690). It can be concluded from the above findings that limited secondary infarct expansion to contribute to the improved cardiac function after infarct.

Thus, the above findings support that endogenous cardiac regeneration significantly contributes to adult cardiac remodeling upon stress in addition to other mechanisms previously recognized as adult cardiomyocyte apoptosis or hypertrophy.

What we claim is:

1. A method for differentiating resident cardiac precursor cells comprising:
   administering to a subject in need thereof comprising said resident cardiac precursor cells, an inhibitor of β-catenin expression or activity or a modulator downregulating β-catenin expression or activity in an β-catenin expression or activity downregulating effective amount,
   wherein the administration is targeted towards cardiac cells or tissues, and
   wherein said administration results in enhanced differentiation of said resident cardiac precursor cells and subsequent regeneration of cardiac tissue.

2. The method of claim 1, wherein the inhibitor or modulator is an expression construct.

3. The method of claim 2, wherein the expression construct encodes protein(s) inhibiting or downregulating β-catenin expression or activity.

4. The method of claim 3, wherein the encoded protein is Axin, Axin2, Chibby, Dapper, Human naked cuticle, Frizzled A, Dickkopf, Nemo-like Ligase, Krüppel-Like-Factors, or Inhibitor of β-catenin (ICAT).

5. The method of claim 2, wherein the expression construct is targeted to β-catenin expression controlling elements.

6. The method of claim 5, wherein the expression controlling elements are deoxyribonucleic acid sequences controlling β-catenin gene transcription.

7. The method of claim 2, wherein the expression construct is a plasmid.

8. The method of claim 2, wherein the expression construct is an adenoviral vector, an adenoassociated vector, a retroviral vector or a lentiviral vector.

9. The method of claim 2, wherein the expression construct is for in vivo gene targeting.

10. The method of claim 9, wherein the in vivo gene targeting is mediated through expression of small interference RNA targeted to β-catenin RNA.

11. The method of claim 2, wherein the expression construct is covalently linked to signaling elements specific for cardiac cells or tissue.

12. The method of claim 2, wherein the expression construct comprises expression control elements specific for cardiac cells or tissues.

13. The method of claim 12, wherein the expression control elements are inducible.

14. The method of claim 1, wherein the inhibitor or modulator is 13-cis-retinoic-acid.

15. The method of 1, wherein the inhibitor or modulator is indometacin.

16. The method of 1, wherein the inhibitor or modulator is PKF 118-310.

17. The method of 1, wherein the inhibitor or modulator is Celecoxib.

18. The method of 1, wherein the inhibitor or modulator is SKI-606.

19. The method of 1, wherein the inhibitor or modulator is Quercitin.

20. The method of 1, wherein the inhibitor or modulator is selected from the group of proteins, peptides, antibodies, nucleic acids and small molecules.

21. The method of claim 20, wherein the inhibitor or modulator is KLF15.

22. The method of 1, wherein the inhibitor or modulator is encapsulated in a carrier targeted to cardiac cells or tissues.

23. The method of 2, wherein the expression construct is encapsulated in a carrier targeted to cardiac cells or tissues.

24. The method of claim 22, wherein a supersonic pulse releases the inhibitor or modulator from the carrier.

25. The method of claim 23, wherein a supersonic pulse releases the expression construct from the carrier.

26. The method of claim 4, wherein the encoded protein is KLF15.

* * * * *